US010383526B2

(12) United States Patent
Batchinsky et al.

(10) Patent No.: US 10,383,526 B2
(45) Date of Patent: Aug. 20, 2019

(54) PATIENT CARE RECOMMENDATION SYSTEM

(75) Inventors: Andriy Batchinsky, San Antonio, TX (US); Leopoldo C. Cancio, San Antonio, TX (US); Jose Salinas, San Antonio, TX (US)

(73) Assignee: United States Government as represented by the Secretary of the Army, Fort Detrick, MD (US)

( * ) Notice: Subject to any disclaimer, the term of this patent is extended or adjusted under 35 U.S.C. 154(b) by 300 days.

(21) Appl. No.: 13/204,502

(22) Filed: Aug. 5, 2011

(65) Prior Publication Data

US 2015/0157213 A1  Jun. 11, 2015

Related U.S. Application Data

(60) Provisional application No. 61/371,614, filed on Aug. 6, 2010.

(51) Int. Cl.
*A61B 5/00* (2006.01)
*A61B 5/08* (2006.01)
(Continued)

(52) U.S. Cl.
CPC .......... *A61B 5/0205* (2013.01); *A61B 5/0022* (2013.01); *A61B 5/0402* (2013.01); *A61B 5/08* (2013.01); *A61B 5/7257* (2013.01); *A61B 5/7275* (2013.01); *G06F 19/3418* (2013.01); *G16H 50/20* (2018.01); *A61B 5/021* (2013.01); *A61B 5/024* (2013.01); *A61B 5/0245* (2013.01);
(Continued)

(58) Field of Classification Search
CPC ..... A61B 5/021; A61B 5/0205; A61B 5/0452; A61B 5/0456
See application file for complete search history.

(56) References Cited

U.S. PATENT DOCUMENTS 4,757,825 A  7/1988  Diamond
4,832,038 A  5/1989  Arai et al.
(Continued)

FOREIGN PATENT DOCUMENTS

WO  WO 2007117402 A2  10/2007
WO  WO2009/136341 A2 * 11/2009 ............... A61B 5/00

OTHER PUBLICATIONS

Yasuma, Fumihiko; Hayano, Jun-Ichiro; *Respiratory Sinus Arrhythmia—Why Does the Heartbeat Synchronize With Respiratory Rhythm?*, Feb. 2004, 125: pp. 683-690, Chest the Cardiopulmonary and Critical Care Journal, American College of Chest Physicians.
(Continued)

*Primary Examiner* — Tiffany Weston
*Assistant Examiner* — Tho Q Tran
(74) *Attorney, Agent, or Firm* — Elizabeth Arwine, Esq.

(57) ABSTRACT

Disclosed are systems and methods to provide a patient care recommendation. The systems and methods receive patient information and a plurality of patient physiological signals that are related to a patient. The systems and methods are then operable to produce at least one derived patient signal from at least one of the plurality of patient physiological signals. The systems and methods use the patient information, at least one of the plurality of patient physiological signals, and the at least one derived patient signal to provide at least one patient care recommendation.

22 Claims, 9 Drawing Sheets

(51) Int. Cl.
  *A61B 5/024*   (2006.01)
  *A61B 5/0245*  (2006.01)
  *A61B 5/0402*  (2006.01)
  *G16H 50/20*   (2018.01)
  *A61B 5/0205*  (2006.01)
  *G06F 19/00*   (2018.01)
  *A61B 5/021*   (2006.01)
  *A61B 5/1455*  (2006.01)

(52) U.S. Cl.
  CPC ......... *A61B 5/0816* (2013.01); *A61B 5/14551* (2013.01); *A61B 5/7228* (2013.01); *A61B 5/7278* (2013.01); *A61B 5/7282* (2013.01); *A61B 5/742* (2013.01); *A61B 5/746* (2013.01)

(56) References Cited

U.S. PATENT DOCUMENTS

| | | | |
|---|---|---|---|
| 4,862,361 A | 8/1989 | Gordon et al. | |
| 5,230,346 A | 7/1993 | Leuchter et al. | |
| 5,259,390 A | 11/1993 | MacLean | |
| 5,299,119 A * | 3/1994 | Kraf | A61B 5/0452 128/905 |
| 5,320,109 A | 6/1994 | Chaumon et al. | |
| 5,433,223 A | 7/1995 | Moore-Ede et al. | |
| 5,566,067 A | 10/1996 | Hobson et al. | |
| 5,568,127 A | 10/1996 | Bang | |
| 5,570,698 A | 11/1996 | Liang | |
| 5,585,785 A | 12/1996 | Gwin | |
| 5,595,488 A | 1/1997 | Gozlan | |
| 5,647,633 A | 7/1997 | Fukuoka | |
| 5,682,144 A | 10/1997 | Mannik | |
| 5,689,241 A | 11/1997 | Clarke, Sr. et al. | |
| 5,691,693 A | 11/1997 | Kithil | |
| 5,813,993 A | 9/1998 | Kaplan et al. | |
| 6,047,203 A | 4/2000 | Sackner et al. | |
| 6,293,915 B1 | 9/2001 | Amano et al. | |
| 6,582,380 B2 | 6/2003 | Kazlausky et al. | |
| 7,855,177 B1 * | 12/2010 | Wahren | A61K 38/28 514/1.1 |
| 7,899,687 B2 | 3/2011 | Morris | |
| 8,273,035 B2 | 9/2012 | Russo et al. | |
| 8,285,372 B2 | 10/2012 | Sing | |
| 8,510,129 B2 | 8/2013 | Morris | |
| 8,682,692 B2 | 3/2014 | Morris | |
| 2001/0029319 A1 | 10/2001 | Kazlausky et al. | |
| 2001/0056225 A1 | 12/2001 | DeVito | |
| 2002/0017994 A1 | 2/2002 | Balkin et al. | |
| 2002/0183644 A1 | 12/2002 | Levendowski et al. | |
| 2003/0092975 A1 | 5/2003 | Casscells, III et al. | |
| 2003/0135126 A1 | 7/2003 | Kuo | |
| 2003/0144572 A1 | 7/2003 | Oschman et al. | |
| 2004/0019289 A1 | 1/2004 | Ross | |
| 2004/0059212 A1 | 3/2004 | Abreu | |
| 2004/0087865 A1 | 5/2004 | Kelly | |
| 2004/0111033 A1 | 6/2004 | Oung et al. | |
| 2004/0181159 A1 | 9/2004 | Kuo et al. | |
| 2005/0096557 A1 | 5/2005 | Vosburgh et al. | |
| 2005/0131738 A1 | 6/2005 | Morris | |
| 2005/0143671 A1 | 6/2005 | Hastings et al. | |
| 2005/0251056 A1 * | 11/2005 | Gribkov | A61B 5/0452 600/509 |
| 2005/0261557 A1 | 11/2005 | Baker | |
| 2006/0100534 A1 | 5/2006 | Colombo et al. | |
| 2006/0217603 A1 | 9/2006 | Nagai et al. | |
| 2007/0112275 A1 | 5/2007 | Cooke et al. | |
| 2008/0221401 A1 | 9/2008 | Derchak et al. | |
| 2009/0024176 A1 * | 1/2009 | Yun et al. | 607/20 |
| 2009/0069642 A1 | 3/2009 | Gao | |
| 2009/0105550 A1 * | 4/2009 | Rothman et al. | 600/300 |
| 2009/0149723 A1 | 6/2009 | Krauss et al. | |
| 2009/0203972 A1 | 8/2009 | Heneghan et al. | |
| 2010/0057490 A1 * | 3/2010 | Kocis et al. | 705/2 |
| 2010/0179438 A1 * | 7/2010 | Heneghan | A61B 5/0205 600/484 |
| 2010/0316158 A1 * | 12/2010 | Arne | 375/285 |
| 2011/0054277 A1 * | 3/2011 | Pinter et al. | 600/310 |
| 2011/0190192 A1 * | 8/2011 | Wahren | 514/1.1 |
| 2013/0013341 A1 | 1/2013 | Morris | |
| 2014/0249430 A1 | 9/2014 | Sims et al. | |

OTHER PUBLICATIONS

Batchinsky, Andriy MD et al; *Prehospital Loss of R-to-R Interval Complexity is Associated With Mortality in Trauma Patients*, Sep. 2007; 63: pp. 512-518, The Journal of Trauma Injury, Infection, and Critical Care, Lippincott Williams & Wilkins.

Batchinsky, Andriy MD et al.; *Loss of Complexity Characterizes the Heart Rate Response to Experimental Hemorrhagic Shock in Swine*, 2007, vol. 35, No. 2, pp. 519-525, Crit Care Med, Society of Critical Care Medicine and Lippincott Williams & Wilkins.

Cancio, Leopoldo MD et al; *Heart-Rate Complexity for Prediction of Prehospital Lifesaving Interventions in Trauma Patients*, Oct. 2008: 65: pp. 813-819, The Journal of Trauma Injury, Infection, and Critical Care, Lippincott Williams & Wilkins.

Eckberg, Dwain; *Point: Counterpoint: Respiratory Sinus Arrhythmia is Due to a Central Mechanism vs. Respiratory Sinus Arrhythmia is Due to the Baroreflex Mechanism*, May 2009, 106: pp. 1740-1742, Journal of Applied Physiology, The American Physiological Society.

White, Christopher E. MD et al; *Lower Interbreath Interval Complexity is Associated With Extubation Failure in Mechanically Ventilated Patients During Spontaneous Breathing Trials*, Jun. 2010; 68: pp. 1310-1316, The Journal of Trauma Injury, Infection, and Critical Care, Lippincott Williams & Wilkins.

Akselrod, Solange, et al., "Power Spectrum Analysis of Heart Rate Fluctuation: A Quantitative Probe of Beat-to-Beat Cardiovascular Control," Science, Jul. 10, 1981, p. 220-22, vol. 213.

Anderer, Peter, et al., "An E-Health Solution for Automatic Sleep Classification according to Rechtschaffen and Kales: Validation Study of the Somnolyzer 24×7 Utilizing the Siesta Database," Neuropsychobiology, Apr. 18, 2005, pp. 115-133, vol. 51.

Baillard, Christophe, et al., "Brain death assessment using instant spectral analysis of heart rate variability," Crit Care Med, 2002, p. 306-310., vol. 30, No. 2.

Brasel, Karen J., et al., "Heart Rate: Is It Truly a Vital Sign?", The Journal of Trauma Injury, Infection, and Critical Care, Apr. 2007, pp. 812-817, vol. 62, No. 4.

Chemla, Denis, et al., "Total arterial compliance estimated by stroke volume-to-aortic pulse pressure ratio in humans," American Journal of Physiology, 1998, p. H500-H505, vol. 274.

Cole, Roger J., et al., "Technical Note Automatic Sleep/Wake Identification from Wrist Activity", Sleep, 1992, pp. 461-469, vol. 5, No. 5, American Sleep Disorders Association and Sleep Research Society.

Convertino, Victor A., et al., "Advanced Diagnostics for the Combat Medic," Army Medical Department Journal, Jul.-Sep. 2003, p. 42-48.

Convertino, Victor A., et al., "Stroke volume and sympathetic responses to lower-body negative pressure reveal new insight into circulatory shock in humans," Autonomic Neuroscience: Basic and Clinical, 2004, p. 127-134, vol. 111.

Convertino, Victor A., et al., "Physiological and Medical Monitoring for En Route Care of Combat Casualties", The Journal of Trauma Injury, Infection, and Critical Care, Apr. 2008, pp. S342-S353, vol. 64, No. 4.

Cooke, William H., "Tropical anesthetic before microneurography decreases pain without affecting sympathetic traffic," Autonomic Neuroscience: Basic and Clinical, 2000, p. 120-126, vol. 86.

Cooke, William H., et al., "Autonomic Neural Control Predicts Hemorrhage Severity and Injury Outcome," presentation at Advanced Technology Applications for Combat Casualty Care conference, Aug. 18, 2004.

Cooke, William H., et al., "Controlled breathing protocols probe human autonomic cardiovascular rhythms," American Journal of Physiology, 1998, p. H709-H718, vol. 274.

(56) References Cited

OTHER PUBLICATIONS

Cooke, William H., et al., "Human responses to upright tilt: a window on central automatic integration," The Journal of Physiology, 1999, p. 617-628, vol. 517.

Cooke, William H., et al., "Lower body negative pressure as a model to study progression to acute hermorrhagic shock humans," J. Appl Physiol, Apr. 2004, p. 1249-1261, vol. 96.

Cooke, William H., et al., "Heart Rate Variability and Its Association with Mortality in Prehospital Trauma Patients", The Journal of Trauma Injury, Infection, and Critical Care, Feb. 2006, pp. 363-370, vol. 60, No. 2.

Dement, William, et al., "Cyclic Variations in EEG during Sleep and Their Relation to Eye Movement, Body, Motility, and Dreaming", Electroencephalography Clin Neurophysciology, Jun. 3, 1957, pp. 673-690, vol. 9.

Elsmore, T. F., et al., "Monitoring Activity with a Wrist-Worn Actigraph: Effects of Amplifier Passband and Threshold Variations", Naval Health Research Center, Technical Report No. 93-18, pp. 1-63, Jan. 14, 1194.

Franklin, Glen A., et al., "Prehospital Hypotension as a Valid Indicator of Trauma Team Activation," The Journal of Trauma: Injury, Infection, and Critical Care, 200, p. 1034-1030, vol. 48, No. 6.

Gravatte, E., "Advanced Respiration Technology a Critical Component of the Warfighter Physiological Status Monitor System," http://www.vivometrics.com/site/press_pr20040525.html, printed on Aug. 15, 2006.

Grogan, Eric L., et al., "Volatility: A New Vital Sign Identified Using a Novel Bedside Monitoring Strategy," The Journal of Trauma: Injury, Infection, and Critical Care, 2005, p. 7-14, vol. 58, No. 1.

Kaplan, R.F, "An Innovative EEG Based Approach to Drowsiness Detection", Department of Systems and Control Engineering, Case Western Reserve University, May 1996, pp. 1-242.

Kelly, Tamsin Lisa, et al., "The Effects of a Single Dose of Pemoline on Performance and Mood During Sleep Deprivation", Military Psychology, pp. 213-225, vol. 9, No. 3.

Lawlor, Maryann, "Personnal Physiological Monitors Find Warfighter-Effectiveness Edge," Signal, Aug. 2000, p. 47-50.

Lee, Jangwoen, et al., "Tissue Hemoglobin Monitoring of Progressive Central Hypovolemia in Humans using Broadband Diffuse Optical Spectroscopy", Journal of Biomedical Optics, Nov./Dec. 2008, pp. 064027-1-064027-10, vol. 13, No. 6.

Rechtschaffen, Allan, et al., "A Manual of Standardized Terminology, Techniques and Scoring System for Sleep Stages of Human Subjects," U.S. Department of Health, Education, and Welfare, Public Health Service—National Institutes of Health, 1968 (reprinted 1971), pp. 1-58.

Redmond, Daniel P., et al., "Observation on the Design and Specification of a Wrist-Worn Human Activity Monitoring System", Behavior Research Methods, Instruments & Computers, 1985, pp. 659-669, vol. 17, No. 6.

Rothisberger, Brian, et al., "Spontaneous 'baroreflex sequences' occur as deterministic functions of breathing phase", 2003, Clinical Physiology and Functional Imaging, 23, pp. 307-313.

Russo, Michael B., et al., "Warfighter Biovibrations", Army Medical Department Journal, Apr.-Jun. 2004, pp. 24-29.

Russo, M. B., "Human Biovibrations: Assessment of Human Life Signs, Motor Activity, and Cognitive Performance Using Wrist-Mounted Actigraphy", Aviation, Space and Environmental Medicine, Jul. 2005, vol. 76, No. 7, Section II, pp. C64-C74.

Sadeh, Avi, et al., "The Role of Actigraphy in the Evaluation of Sleep Disorders", Sleep, 1995, pp. 288-302, vol. 18, No. 4, American Sleep Disorders Association and Sleep Research Society.

Sethuraman, Girish, et al., "Ectopy in Trauma Patients: Cautions for Use of Heart Period Variability in Medical Monitoring", Aviation, Space, and Environmental Medicine, Feb. 2010, pp. 125-129, vol. 81, No. 2.

Sing, Helen C., et al., "High-Frequency EEG as Measure of Cognitive Function Capacity: A Preliminary Report," Aviation, Space, and Environmental Medicine, Jul. 2005, pp. C114-C135, vol. 76, No. 7, Section II.

Sing, Helen C., "Chapter 14 High Frequency EEG and Its Relationship to Cognitive Function", Lloyd et al. (eds.), Ultradian Rhythms from Molecules to Mind, 2008, pp. 303-341.

Thompson, Cynthia A., "Baroreflex responses to acute changes in blood volume in human," American Journal of Physiology, 1990, p. R792-R798, vol. 259.

Webster John, B., et al., "An Activity-Based Sleep Monitor System for Ambulatory Use", Sleep, 1982, pp. 389-399, vol. 5, No. 4.

Winchell, Robert J., et al., "Analysis of Heart-Rate Variability: A Noninvasive Predictor of Death and Poor Outcome in Patients with Severe Head Injury," The Journal of Trauma: Injury, Infection, and Critical Care, Aug. 1997, p. 927-933, vol. 43, No. 6.

Winchell, Robert J., et al., "Spectral Analysis of Heart Rate Variability in the ICU: A Measure of Autonomic Function," Journal of Surgical Research, Jun. 1996, p. 11-16, Article No. 0214, vol. 63, No. 1.

Sethuraman, G., et al., "Ectopic Beats in Healthy Humans and Trauma Patients: Limitations for Use of Heart Period Variability Indices in Medical Monitoring", Advanced Technology Applications for Combat Casualty Care conference, poster presentation, Aug. 10-12, 2009.

Cooke, William H., et al., "Inappropriate Parasympathetic Predominance is Revealed with Prehospital Frequency-Domain Anaylsis of Heart Rate Variability", Advanced Technology Applications for Combat Casualty Care conference, poster presentation, 2006.

Baron, R. and Ewing, D.J., "Chapter 7.2: Heart rate variability," Guidelines of the International Federation of Clinical Neurophysiology, 1999, pp. 283-286, Elsevier Science.

Holcomb, J., et al., "Prehospital Physiologic Data and Lifesaving Intervention in Trauma Patients," Military Medicine, 2005, pp. 7-13, vol. 170, 1:7, Association of Military Surgeons of the U.S.

National Institutes of Health/ National Institute on Aging, "Heart Health," National Institutes of Health, pp. 1-7, printed on Apr. 11, 2016 from https://www.nia.nih.gov/health/publication/heart-health.

National Institutes of Health/ U.S. National Library of Medicine: "Aging Changes in vital signs," MedlinePlus, pp. 1-3, MedlinePlus Encyclopedia, printed on Apr. 12, 2016 from https://www.nlm.nih.gov/medlineplus/ency/article/004019.htm.

U.S. Patent and Trademark Office, Office Action in U.S. Appl. No. 13/204,490 dated Nov. 19, 2015.

* cited by examiner

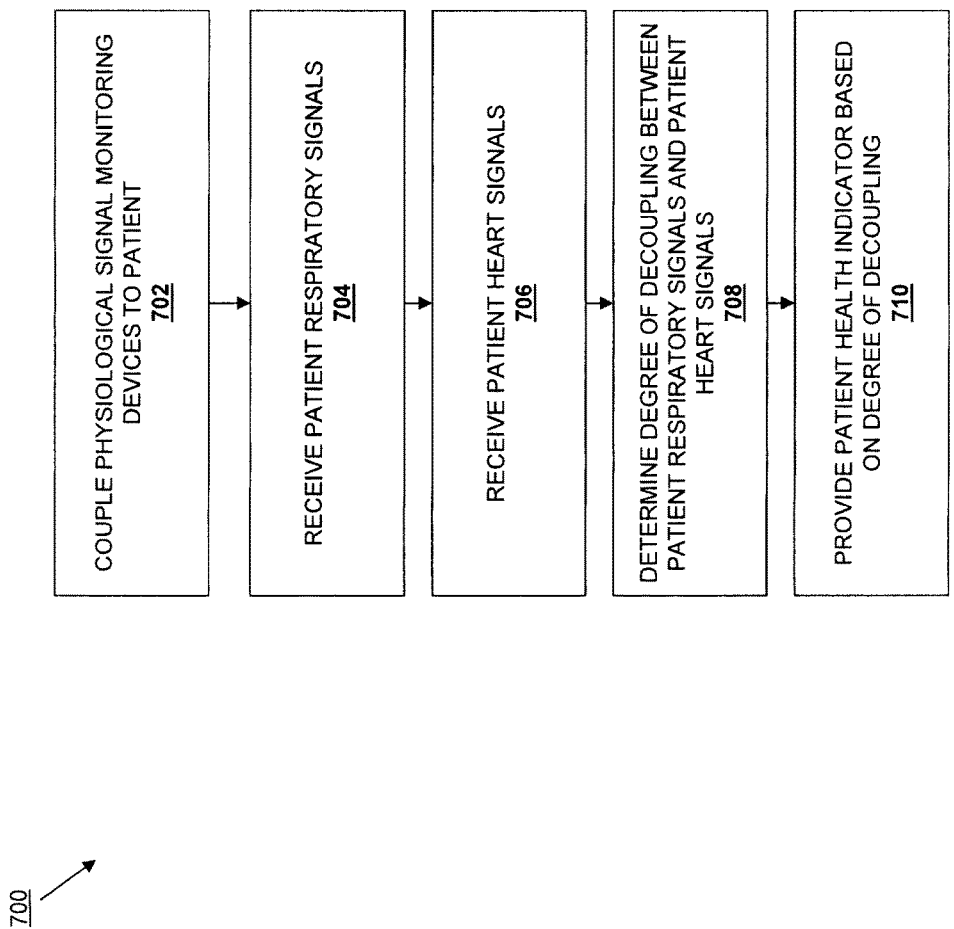

PATIENT CARE RECOMMENDATION SYSTEM

CROSS REFERENCE TO RELATED APPLICATIONS

This present application claims priority to U.S. Provisional Application Ser. No. 61/371,614, filed on Aug. 6, 2010, and is related to U.S. application Ser. No. 13/204,490, filed on Aug. 5, 2011 and U.S. application Ser. No. 13/204,460, filed on Aug. 5, 2011.

This invention was made with government support under Contract No. W81XWH-07-C-0059 awarded by the U.S. Army Institute of Surgical Research, Fort Sam, Houston. The government has certain rights in the invention.

FIELD OF THE DISCLOSURE

Various embodiments of the disclosure pertain to a system and method to provide a care recommendation for a patient, and more particularly to a system and method for quickly and accurately providing a life saving intervention (LSI) recommendation for a patient in a critical condition.

BACKGROUND

Triage and diagnosis of patients can be problematic due to a lack of knowledge about the condition or status of the patient. Current physiological monitoring is confined to limited sets of conventional non-invasive measurements of physiological signs of the patient throughout the pre-hospital care phase such as, for example, heart rate, blood pressure, respiratory rate, and oxygen saturation. Due to this limited information, treatment options are not based on empirical data, but rather typically rely on the experience of the patient care provider and the limited measurements of physiological signs available from the patients. Consequently, critical decisions may be made based on incomplete knowledge of the patient condition.

Furthermore, when dealing with multiple patients in a pre-hospital or hospital situation, the lack of accurate data becomes problematic when decisions on patient care prioritization and treatment options must be made for several patients in a short time frame. Thus, many patient care decisions may be incorrect and/or delayed.

Patient care decisions are further complicated by human compensatory mechanisms that result in adequate blood flow to the patient's core and head that can mask the patients true condition, as the conventional physiological signs that are used to determine the status of the patient do not take into account, and may even disregard, those compensatory mechanisms.

Accordingly, it is desirable to provide an improved system and method for making patient care decisions.

SUMMARY

Various embodiments of the present disclosure are directed to systems and methods to provide a patient care recommendation. The systems and methods provide techniques to receive patient information, receive a plurality of patient physiological signals that are related to a patient, produce at least one derived patient signal from at least one of the plurality of patient physiological signals, and provide at least one patient care recommendation using the patient information, at least one of the plurality of patient physiological signals, and the at least one derived patient signal.

BRIEF DESCRIPTION OF THE DRAWINGS

FIG. 7 is a flow chart illustrating an embodiment of a method for providing a patient health indicator/derived patient signal.

DETAILED DESCRIPTION

Figure 1:
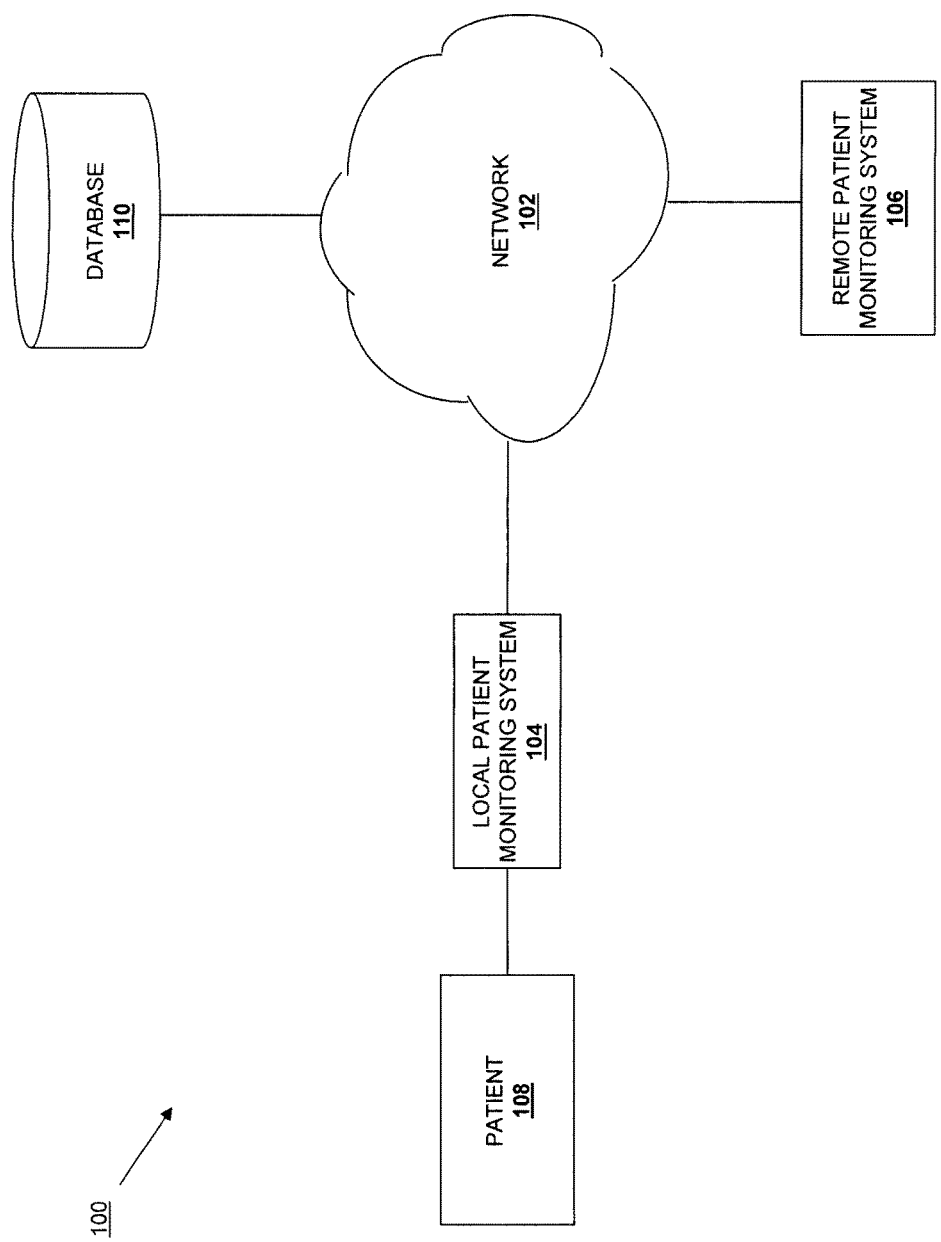
FIG. 1 is a schematic view illustrating an embodiment of a patient care recommendation system.

Referring now to FIG. 1, in one embodiment, a patient care recommendation system 100 is illustrated. The patient care recommendation system 100 includes a network 102 such as, for example, a Transport Control Protocol/Internet Protocol (TCP/IP) network (e.g., the Internet or an intranet). A local patient monitoring system 104 is operably coupled to the network 102. In an embodiment, a remote patient monitoring system 106 may also be operably coupled to the network 102. However, in other embodiments, the remote patient monitoring system 106 may be omitted from the system 100. A patient 108 is coupled to the local patient monitoring system 104. A database 110 may also be coupled to the local patient monitoring system 104 and/or the remote patient monitoring system 106 through the network 102. In an unillustrated embodiment, the database 110 may be included with the local patient monitoring system 104 and/or the remote patient monitoring system 106.

The local patient monitoring system 104 and, in some embodiments, the remote patient monitoring system 106, include a respective network interface for communicating with the network 102 (e.g., outputting information to, and receiving information from, the network 102), such as by transferring information (e.g., instructions, data, signals) between such systems and the network 102. Accordingly, through the network 102, the local patient monitoring system 104 may communicate with the remote patient monitoring system 106, and the remote patient monitoring system 106 may communicate with the local patient monitoring system 104.

For clarity, FIG. 1 depicts only one local patient monitoring system 104. However, one of skill in the art will recognize that the patient care recommendation system 100 may include a plurality of local patient monitoring systems similar to the local patient monitoring system 104 as described below. Likewise, for clarity, FIG. 1 depicts only one remote patient monitoring system 106. However, the patient care recommendation system 100 may include a plurality of remote patient monitoring systems.

Each of the local patient monitoring system 104 and the remote patient monitoring system 106 includes a respective information handling system (IHS), a subsystem, or a part of a subsystem for executing processes and performing operations (e.g., processing or communicating information) in response thereto, as discussed further below. Each such IHS is formed by various electronic circuitry components. Moreover, as illustrated in FIG. 1, all such IHSs may be coupled to each other through the network 102. Accordingly, the local patient monitoring system 104 and the remote patient monitoring system 106 may operate within the network 102.

An IHS is an electronic device capable of processing, executing or otherwise handling information. Examples of an IHS include a server computer, a personal computer (e.g., a desktop computer or a portable computer such as, for example, a laptop computer), a handheld computer, a wearable computer (as discussed in further detail below), and/or a variety of other computers known in the art.

Figure 2:
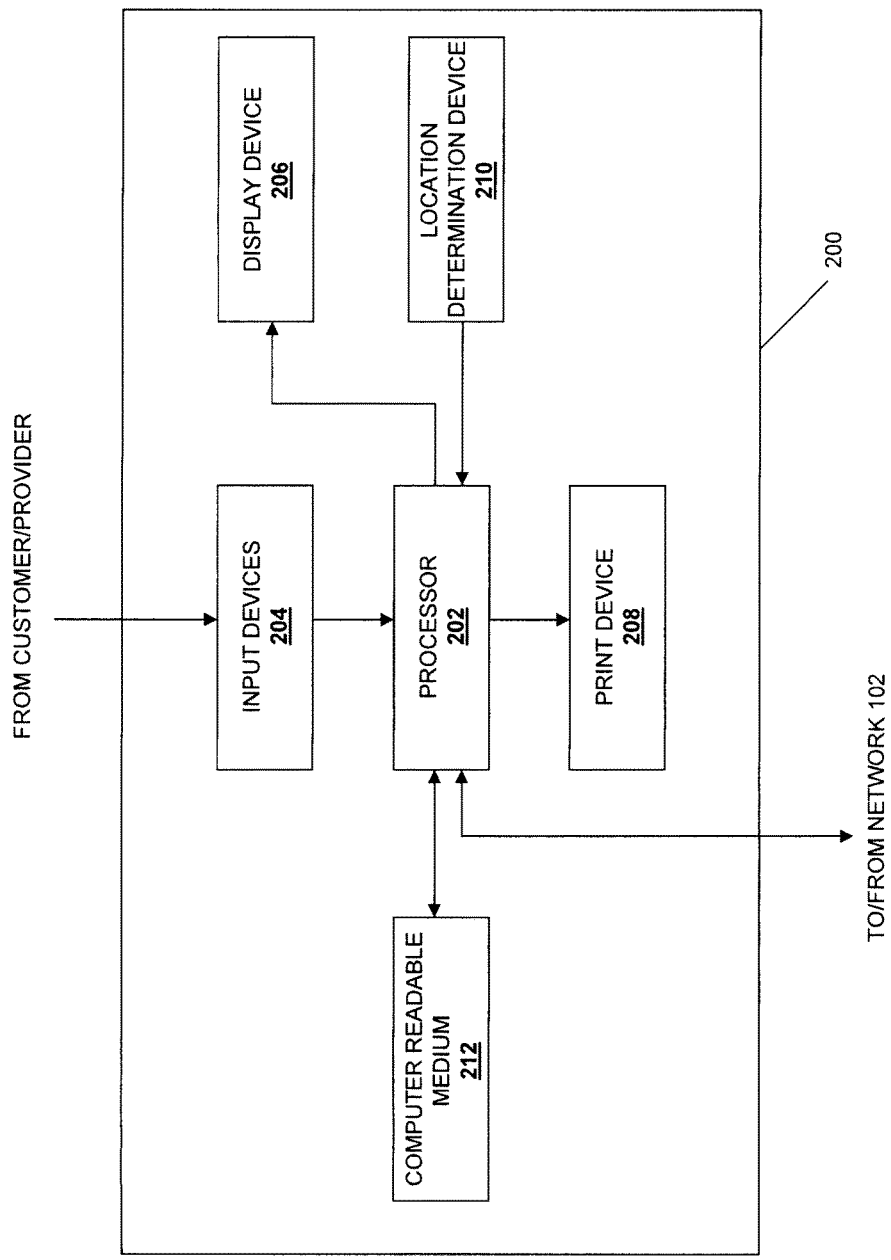
FIG. 2 is a schematic view illustrating an embodiment of an information handling system used with the patient care recommendation system.

Referring now to FIG. 2, an IHS 200 which is representative of one of the IHSs described above, is illustrated. The IHS 200 may include any or all of the following: (a) a processor 202 for executing and otherwise processing instructions, (b) a plurality of input devices 204, which are operably coupled to the processor 202, for inputting information, (c) a display device 206 (e.g., a conventional electronic cathode ray tube (CRT) device or a conventional liquid crystal display (LCD)), which is operably coupled to the processor 202, for displaying information, (d) a print device 208 (e.g. a conventional electronic printer or plotter), which is operably coupled to the processor 202, for printing visual images (e.g., textual or graphic information on paper), scanning visual images, and/or faxing visual images, (e) a location determination device 210 (e.g., a Global Positioning System (GPS) device, a cell tower triangulation device, etc.) for determining a location of the IHS 200, (f) a computer-readable medium 212, which is operably coupled to the processor 202, for storing information, as discussed further below, (f) various other electronic circuitry for performing other operations of the IHS 202 known in the art, and/or a variety of other IHS components known in the art.

For example, the IHS 200 may include (a) a network interface (e.g., circuitry) for communicating between the processor 202 and the network 102 and (b) a memory device (e.g., a random access memory (RAM) device or a read-only memory (ROM) device for storing information (e.g., instructions executed by processor 114 and data operated upon by processor 202 in response to such instructions)). Accordingly the processor 202 is operably coupled to the network 102, the input devices 204, the display device 206, the print device 208, the location determination device 210, and the computer-readable medium 212, as illustrated in FIG. 2.

For example, in response to signals from the processor 202, the display device 206 displays visual images. Information may be input to the processor 202 from the input devices 204 (discussed in further detail below), and the processor 202 may receive such information from the input devices 204. Also, in response to signals from the processor 202, the print device 208 may print visual images on paper, scan visual images, and/or fax visual images.

The input devices 204 include a variety of input devices known in the art such as, for example, a conventional electronic keyboard and a pointing device such as, for example, a conventional electronic mouse, trackball, or light pen. The keyboard may be operated to input alphanumeric text information to the processor 202, and the processor 202 may receive such alphanumeric text information from the keyboard. The pointing device may be operated to input cursor-control information to the processor 202, and the processor 202 may receive such cursor-control information from the pointing device. The input devices 204 may also include a variety of physiological signal monitoring devices, as described in further detail below.

The computer-readable medium 212 and the processor 202 are structurally and functionally interrelated with one another as described below in further detail. Each IHS of the illustrative embodiment is structurally and functionally interrelated with a respective computer-readable medium, similar to the manner in which the processor 202 is structurally and functionally interrelated with the computer-readable medium 212. In that regard, the computer-readable medium 212 is a representative one of such computer-readable media including, for example, but not limited to, memory, a hard disk drive, a solid state memory device, and/or a variety of other computer-readable media known in the art.

The computer-readable medium 212 stores (e.g., encodes, records, or embodies) functional descriptive material (e.g., including but not limited to software (also referred to as computer programs or applications) or data structures). Such functional descriptive material imparts functionality when encoded on the computer-readable medium 212. Also, such functional descriptive material is structurally and functionally interrelated to the computer-readable medium 212.

With such functional descriptive material, data structures define structural and functional interrelationships between such data structures and the computer-readable medium 212 (and other aspects of the patient care recommendation system 100). Such interrelationships permit the data structures' functionality to be realized. Also, within such functional descriptive material, computer programs define structural and functional interrelationships between such computer programs and the computer-readable medium 212 (and other aspects of the patient care recommendation system 100). Such interrelationships permit the computer programs' functionality to be realized.

For example, the processor 202 reads (e.g., accesses or copies) such functional descriptive material from the computer-readable medium 212 onto the memory device of the IHS 200, and the IHS 200 (more particularly, the processor 202) performs its operations, as described elsewhere herein, in response to such material which is stored in the memory device of the IHS 200. More particularly, the processor 202 performs the operation of processing a computer application (that is stored, encoded, recorded, or embodied on a computer-readable medium) for causing the processor 202 to perform additional operations, as described elsewhere herein. Accordingly, such functional descriptive material exhibits a functional interrelationship with the way in which processor 202 executes its processes and performs its operations.

Further, the computer-readable medium 212 is an apparatus from which the computer application is accessible by the processor 202 for instructing the processor 202 to perform such additional operations. In addition to reading such functional descriptive material from the computer-readable medium 212, the processor 202 is capable of reading such functional descriptive material from (or through) the network 102. Moreover, the memory device of the IHS 200 is itself a computer-readable medium (or apparatus).

Figure 3:
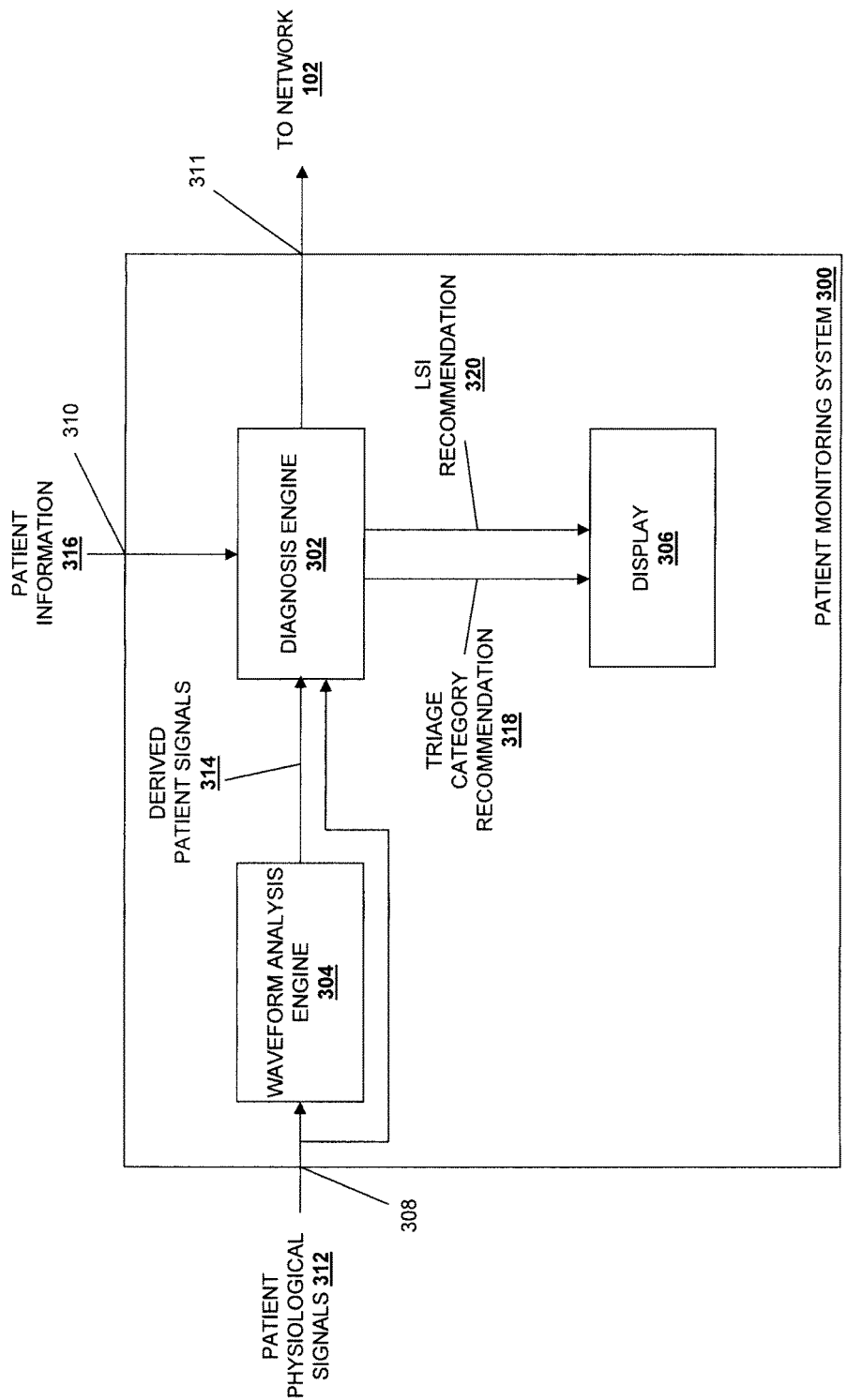
FIG. 3 is a schematic view illustrating an embodiment of a patient monitoring system used in the patient care recommendation system.

Referring now to FIG. 3, a patient monitoring system 300, which may be the local patient monitoring system 104 and/or the remote patient monitoring system 106, discussed above with reference to FIG. 1, is illustrated in more detail. The patient monitoring system 300 includes a diagnosis engine 302 that may be provided by a processor (e.g., the processor 202 discussed above with reference to FIG. 2) and instructions that are stored on a computer-readable medium that is coupled to the processor (e.g., the computer-readable medium 212 discussed above with reference to FIG. 2). A waveform analysis engine 304 is coupled to the diagnosis engine 302 and may be provided by a processor (e.g., the processor 202 discussed above with reference to FIG. 2) and instructions that are stored on a computer-readable medium that is coupled to the processor (e.g., the computer-readable medium 212 discussed above with reference to FIG. 2). A display 306, which may be the display 206 discussed above with reference to FIG. 2, is coupled to the diagnosis engine 302. At least one patient physiological signal input 308 is included on the patient monitoring system 300 and coupled to the diagnosis engine 302 and the waveform analysis engine 302. At least one patient information input 310 is included on the patient monitoring system 300 and coupled to the diagnosis engine 302. At least one network input/output 311 is included on the patient monitoring system 300 and coupled to the diagnosis engine 302.

Referring now to FIGS. 1 and 3, the patient care recommendation system 100 may include a number of different embodiments for providing patient care recommendations for the patient 108. For example, in one embodiment, the local patient monitoring system 104 of FIG. 1 may be the patient monitoring system 300 of FIG. 3, and patient physiological signals 312 from the patient 108 may be used, at least in part, to provide the patient care recommendation (e.g., on the display 306), as described in further detail below. In another embodiment, the remote patient monitoring system 106 of FIG. 1 may be the patient monitoring system 300 of FIG. 3, and patient physiological signals 312 from the patient 108 may be sent by the local patient monitoring system 104 over the network 102 to the remote patient monitoring system 106. The remote patient monitoring system 106 may then use the patient physiological signals 312, at least in part, to provide the patient care recommendation (e.g., on the display 306, by sending that patient care recommendation over the network 102 to an IHS or other communications device, etc.), as described in further detail below. While a few embodiments of the patient care recommendation system 100 are illustrated and described, one of skill in the art will recognize that a variety of modifications to the patient care recommendation system 100 as described below will fall within the scope of the present disclosure.

As discussed above, the waveform engine 304 may be provided by a processor and instructions that are stored on a computer-readable medium that is coupled to the processor. In one embodiment, the waveform analysis engine 304 is coupled to the at least one patient physiological signal input 308 and operable to retrieve and/or receive at least one patient physiological signal 312 from at least one physiological signal monitoring device that is coupled to the patient monitoring system 300 through the at least one patient physiological signal input 308 (e.g., a device coupled directly to the input 308, a device coupled to the input 308 over the network 102, etc.). For example, the waveform analysis engine 304 may be operable to retrieve and/or receive patient heart signals (e.g., heart rate signals) from a heart monitoring device that is coupled to the at least one patient physiological signal input 308, patient respiratory signals (e.g., respiration rate signals) from a respiratory monitoring device that is coupled to the at least one patient physiological signal input 308, patient blood pressure signals from a blood pressure monitoring device that is coupled to the at least one patient physiological signal input 308, patient electrocardiogram (EKG) signals from an EKG device that is coupled to the at least one patient physiological signal input 308, patient pulse oximetry signals from a finger sensor or other pulse oximetry device that is coupled to the at least one patient physiological signal input 308, and/or a variety of other patient physiological signals from a variety of physiological signal monitoring devices known in the art. One of skill in the art will recognize the patient physiological signals 312 discussed above (e.g., patient heart signals, patient respiratory signals, patient blood pressure signals, patient EKG signals, patient pulse oximetry signals, etc.) as conventional patient vital signs and physiological waveforms known in the art, and that plurality of other patient physiological signals may be collected such as End Tidal $CO_2$ (ETCO2) concentration, oxygen saturation, and/or a variety of other patient physiological signals known in the art. In an embodiment, the patient physiological signal(s) 312 may be retrieved and/or received by the waveform analysis engine 304 continuously and/or in real-time as long as the appropriate physiological signal monitoring devices are operating and attached to the patient 108.

The waveform analysis engine 304 is operable to use those patient physiological signals 312 to produce a plurality of derived patient signals 314. In an embodiment, the derived patient signals 314 may be produced in real-time (e.g., as the real-time physiological signals from the patient are provided to the waveform analysis engine 304). As described below, the derived patient signals 314 may be produced without hands-on contact with the patient (e.g., the derived patient signals 314 may be produced using patient physiological signals generated at a first location and transmitted to a second location that is different from the first location). In an embodiment, the waveform analysis engine 304 may be operable to produce the plurality of derived patient signals 314 by performing linear and/or nonlinear statistical methods such as, for example, nonlinear-dynamics-based statistical analysis of variability and/or complexity in a time series of a patient physiological signals 312 (e.g., the variability and/or complexity of the patient's heart rate signals). For example, such nonlinear statistical methods may include performing a fast Fourier transform on a time series of a patient physiological signal or signals, performing complex demodulation on a time series of a patient physiological signal or signals, determining approximate entropy and/or sample entropy on a time series of a patient physiological signal or signals, determining the similarity of distributions on a time series of a patient physiological signal or signals, performing detrended fluctuations analysis on a time series of a patient physiological signal or signals, performing fractal analysis on a time series of a patient physiological signal or signals, and/or conducting a variety of other nonlinear-dynamics-based statistical analysis known in the art on a time series of a patient physiological signal or signals. In an embodiment, the waveform analysis engine 304 may include or be coupled to systems that enhance signal quality, signal transmission, signal noise filtering, and/or a variety of other signal properties known in the art in order to allow for the linear and nonlinear statistical methods to be performed on the physiological signals and/or to increase the accuracy of those methods.

In one embodiment, the waveform analysis engine 304 is coupled to a EKG device that is coupled to the local patient monitoring system 300 through the at least one patient physiological signal input 308. With the EKG device coupled to a patient (e.g., the patient 108 discussed above with reference to FIG. 1), patient EKG signals are provided through the at least one patient physiological signal input 308 to the waveform analysis engine 304. The waveform analysis engine 304 may then use the patient EKG signals to determine a variety of derived patient signals. For example, time domain derived patient signals may be determined such as RRI, the mean R-to-R interval lengths in milliseconds, and RMSSD, the square root of the mean squared differences of successive normal-to-normal (NN) R-to-R intervals and pNN50 defined as the number of successive NN intervals that differ by more than 50 ms divided by the total number of NN intervals (pNN50). In another example, frequency domain derived patient signals may be determined that include those derived by fast-Fourier transform: the total power of periodic oscillations in the EKG (TP, calculated over 0.003-0.4 Hz), low frequency power (LF, 0.04-0.15 Hz), high-frequency power (HF, 0.15-0.4 Hz,) LF/HF and HF/LF ratios of the signal, values of the signal normalized to TP (LFnu, HFnu, LFnu/HFnu, HFnu/LFnu). In another example, complex demodulation (CDM) derived patient signals may be created using CDM analysis that investigates the low frequency (CDM LF) and high frequency (CDM HF) amplitudes of regular oscillations in the EKG. In another example, heart rate complexity derived patient signals may be determined such as derived signals that measure the irregularity of the signal (e.g., the approximate entropy ApEn and/or sample entropy SampEn of the signal), the fractal dimension of the signal (e.g., using Fractal Dimension by Dispersion Analysis [FDDA] or using Curve Lengths [FDCL]), the autocorrelation of the RRI signal distribution (e.g., using Similarity of Distribution [SOD]), short-term (e.g., 8-10 heartbeats) correlations in the signal by Detrended Fluctuation Analysis (DFA), signal Stationarity (StatAV), and symbolic dynamics analysis such as percentage of forbidden word (FW) and normalized symbol distribution entropy (DisnEn). In another example, derived patient signals may include pulse pressure and/or shock index. While a plurality of examples have been provided of derived patient signals determined or created using an EKG signal, one of skill in the art will recognize that a variety of other derived patient signals may be determined or created using an EKG signal and/or other physiological signal(s) of a patient without departing from the scope of the present disclosure.

In another embodiment, the waveform analysis engine 304 is coupled to each of a respiration monitoring device and a heart monitoring device that are both coupled to the patient monitoring system 300 through the at least one patient physiological signal input 308. With the respiration monitoring device and the heart monitoring device coupled to a patient (e.g., the patient 108 discussed above with reference to FIG. 1), patient respiratory signals (e.g., respiratory rate signals) and patient heart signals (e.g., heart rate signals) of the patient are provided through the at least one patient physiological signal input 308 to the waveform analysis engine 304. The waveform analysis engine 304 may then use the patient respiratory signals and patient heart signals to determine various respiratory sinus arrhythmia (RSA) signals or related signals (i.e., derived patient signals) for the patient. For example, as discussed in further detail below, the waveform analysis engine 304 may calculate the RSA signals as the ratio of an interbeat interval during inspiration to the interbeat interval during expiration. While an example of a calculation of RSA signals for a patient is provided, one of skill in the art will recognize that RSA signals may be calculated using a variety of different methods without departing from the scope of the present disclosure.

As discussed above, the diagnosis engine 302 may be provided by a processor and instructions that are stored on a computer-readable medium that is coupled to the processor. In an embodiment, the diagnosis engine 302 is a machine learning system. For example, the diagnosis engine 302 may include an Artificial Neural Network (ANN) such as a perceptron or other ANN known in the art. In an embodiment, the diagnosis engine 302 may include patient care intelligence that is based on a plurality of trauma patient data and/or other real-world patient data known in the art. For example, the diagnosis engine 302 may be created using trauma patient data from the database 110, discussed above with reference to FIG. 1, to provide the diagnosis engine 302 with patient care intelligence that allows the diagnosis engine 302 to provide patient care recommendations, as discussed in further detail below. In an experimental embodiment, trauma patient data for a plurality of different patients that included patient EKG signals for each patient was used to create a plurality of derived patient signals for each patient, and those derived patient signals were provided to an ANN to determine whether those derived patient signals could be used to identify which patients underwent life saving interventions (LSIs). In this experimental embodiment, it was found that the derived patient signals could be used to identify patients that received an LSI with a significant and clinically relevant degree of accuracy (in one experimental embodiment, the accuracy was 90%). Thus, one of skill in the art will recognize that the diagnosis engine 302 may be created using trauma patient data that may include patient physiological signals (e.g., patient EKG or other signals), derived patient signals (discussed above), and/or other patient information (e.g., patient physical characteristics), along with patient care information (e.g., whether or not the patient received an LSI), to provide or 'teach' the diagnosis engine 302 patient care intelligence that allows the diagnosis engine 302 to provide patient care recommendations, discussed in further detail below.

For example, in one embodiment, an ANN used in the diagnosis engine 302 of the present disclosure may be composed of a set of nodes representing a model of a neural network that has been configured to make decisions on the need for a LSI that is based on a set of patient information, physiological signals, derived signals or vital signs, trends, and/or other states that are provided into the inputs of the nodes. The ANN may use a 3 layer structure with a set of input nodes, a set of hidden nodes, and a set of output nodes that make up the layers of the model. All nodes from the input layer may be fully connected to the hidden layer (e.g., there may be one connection from each input layer to all hidden nodes). Similarly, all hidden nodes may be fully connected to the output layers. As the ANN is provided as a computer model, all nodes and connections may be represented via software data structures for representing network nodes and connections. Nodes in the input, hidden, and output layers take data (e.g., patient physiological signals, derived patient signals, patient information, etc.) from the input side and transform the values using a set of learned weights to generate a set of outputs that correspond to the need for an LSI. The weights of the nodes may be determined using a supervised learning algorithm based on trauma patient data from the database, discussed above. As discussed above, a set of data with known results may be given to the model. The weights of the model may then be adjusted for each case based on the results of the set. In an experimental embodiment, a portion of which is discussed in further detail below, sets of vital signs were fed to the model with the corresponding outcome for the patient (patient received an LSI or patient did not receive an LSI). For each case, the model adjusted the weights of the nodes based on the new dataset it was provided. In this experimental embodiment, the inputs to the model included the patient vital signs for systolic blood pressure (SBP), diastolic blood pressure (DBP), mean blood pressure (MAP), blood oxygen saturation (SpO2), respiratory rate (RR), heart rate (HR), shock index (SI=HR/SBP), and pulse pressure (PP=SBP-DBP), Additionally, inputs also included the trends (i.e. slope of the vital signs over time), and the maximum/minimum values for each of the vital signs. Results of a physical exam were also used for training including the Glasgow Coma Score and the Capillary Refill. Any of these or other values may be used to determine the final weights to use for data processing at each node in the ANN. Once the model has been trained based on the initial dataset, data may be passed to the system for operational use to generate an LSI recommendation and/or probability that a patient will require an LSI based on new data provided to the system. One of skill in the art will recognize that the diagnosis engine 302 including the ANN discussed above may be periodically or continuously updated with trauma patient data in order to supplement, replace, or otherwise enhance the patient care intelligence included in the diagnosis engine 302.

In an experimental embodiment, the table below was produced. The table illustrates the results of trauma patient data analyzed to determine whether a plurality of patient demographic variables, patient conventional vital sign variables, and patient injury score variables are predictive of whether or not a patient receives an LSI:

| Variable | Non LSI (n = 197) | LSI (n = 65) | P value |
| --- | --- | --- | --- |
| Age, yr | 35.3 +/− 0.99 | 33.5 +/− 1.8 | 0.271 |
| Sex (male) | 75.1% | 82.5% | 0.224 |
| MOI (penetrating) | 28.42% | 26.56% | 0.775 |
| HR | 97 +/− 1.6 | 109 +/− 4.3 | 0.004 |
| SAP | 129 +/− 1.7 | 120 +/− 3.6 | 0.03 |
| $GCS_{TOTAL}$ | 14.2 +/− 0.16 | 8.94 +/− 0.7 | <.0001 |
| $GCS_{MOTOR}$ | 5.8 +/− 0.06 | 3.7 +/− 0.32 | <.0001 |
| Mortality | 1.52% | 13.9% | 0.0004 |

As can be seen, LSI patients tended to not differ from non-LSI patients with respect to age, sex, and mechanism of injury (MOI), but tended to have a higher heart rate (HR), a lower Systolic Arterial Pressure (SAP), a lower GCS (Glasgow Coma Score), and a higher mortality.

In an experimental embodiment, the table below was produced. The table illustrates the results of trauma patient data analyzed to determine whether a plurality of linear time and frequency domain patient variable (e.g., derived patient signals) are predictive of whether or not a patient receives an LSI:

| Variable | Non LSI (n = 197) | LSI (n = 65) | P value | Reflects parasympathetic nervous system | Reflects sympathetic nervous system | Predictor of LSI picked by ANN? |
| --- | --- | --- | --- | --- | --- | --- |
| RRI | 650.50 +/− 9.70 | 565.63 +/− 16.19 | <.0001 | Yes | Yes | Yes |
| RRMSD | 13.89 +/− 0.88 | 6.17 +/− 0.77 | <.0001 | Yes | | Yes |
| pNN50 | 3.53 +/− 0.65 | 0.44 +/− 0.18 | <.0001 | Yes | | |
| TP | 1107.75 +/− 131.81 | 305.98 +/− 58.73 | <.0001 | Yes | Yes | Yes |
| LF | 278.18 +/− 25.07 | 58.58 +/− 16.55 | <.0001 | Yes | Yes | |
| HF | 95.57 +/− 13.73 | 21.49 +/− 7.03 | <.0001 | Yes | | Yes |
| LF/HF | 150.04 +/− 104.68 | 104.68 +/− 46.39 | <.0001 | Yes | Yes | |
| HF/LF | 0.31 +/− 0.03 | 0.42 +/− 0.07 | 0.371 | Yes | Yes | Yes |
| LFnu | 0.77 +/− 0.01 | 0.67 +/− 0.02 | <.0001 | Yes | Yes | |
| HFnu | 0.20 +/− 0.01 | 0.25 +/− 0.02 | 0.013 | Yes | | Yes |
| LFnu/HFnu | 6.36 +/− 0.40 | 5.11 +/− 0.73 | 0.002 | Yes | Yes | Yes |
| HFnu/LFnu | 0.34 +/− 0.03 | 0.53 +/− 0.08 | 0.002 | Yes | Yes | |
| CDM LF | 16.22 +/− 0.78 | 5.75 +/− 0.86 | <.0001 | Yes | Yes | Yes |
| CDM HF | 8.28 +/− 0.57 | 3.35 +/− 0.53 | <.0001 | Yes | | Yes |
| CDM LF/HF | 2.40 +/− 0.09 | 1.79 +/− 0.13 | <.0001 | Yes | Yes | Yes |

As can be seen, patients that received an LSI had lower values for all time domain and frequency domain descriptive metrics except for HUnu and HFnu/LFnu (which were higher) and HF/LF (which did not differ.)

Finally, in an experimental embodiment, the table below was produced. The table illustrates the results of trauma patient data analyzed to determine whether a plurality of heart rate complexity analysis data (e.g., derived patient signals) is predictive of whether or not a patient receives an LSI:

| Variable | Non LSI (n = 197) | LSI (n = 65) | P value | Predictor of LSI picked by ANN? |
|---|---|---|---|---|
| ApEn | 1.10 +/− 0.02 | 0.93 +/− 0.04 | <.0001 | Yes |
| SampEn | 1.13 +/− 0.02 | 0.90 +/− 0.04 | <.0001 | |
| FDDA | 1.13 +/− 0.01 | 1.07 +/− 0.01 | <.0001 | |
| DFA | 1.35 +/− 0.03 | 1.07 +/− 0.05 | <.0001 | Yes |
| SOD | 0.15 +/− 0.00 | 0.20 +/− 0.01 | <.0001 | |
| StatAV | 0.82 +/− 0.01 | 0.95 +/− 0.01 | <.0001 | |
| FW | 52.59 +/− 0.93 | 60.84 +/− 1.17 | <.0001 | Yes |
| DisnEn | 0.64 +/0 0.01 | 0.55 +/− 0.01 | <.0001 | Yes |

As can be seen, patients that received an LSI had lower values for these metrics with the exception of Similarity of Distributions (SOD), signal Stationarity (StatAV), and forbidden words (FW), which were higher.

The tables above are provided as an example of how trauma patient data may be used with the diagnosis engine 302, and is not meant to be limit the creation of the diagnosis engine 302 to any particular trauma patient data. Furthermore, as can be seen from the tables, the ANN picked 14 of the derived patient signals as predictors of the need to perform an LSI on the patient. While, in an embodiment, those 14 derived patient signals may be used or deemed useful in the diagnosis engine 302, it does not necessary follow that, in other embodiments, the derived patient signals not picked by the ANN in the experimental embodiment illustrated above would not be provided by the waveform analysis engine 304 or used by the diagnosis engine 302 to provide a patient care recommendation, discussed in further detail below. Furthermore, it should be clear to one of skill in the art that other derived patient signals, combinations of patient information, conventional physiological signals, and derived patient signals, etc. may be used to create the diagnosis engine 302 such that accurate patient care recommendations may be provided. Thus, the tables above are simply an example of one set of trauma data used to prove the concept of a diagnosis engine using derived patient signals to determine the need for an LSI and/or provide an LSI recommendation, and one of skill in the art will recognize that additional information or instructions may be provided to the diagnosis engine 302 of the present disclosure in order for the diagnosis engine 302 to provide patient care recommendations.

The diagnosis engine 302 is coupled to the at least one patient physiological signal input 308 and operable to retrieve and/or receive at least one patient physiological signal 312 from at least one physiological signal monitoring device that is coupled to the patient monitoring system 300 through the at least one patient physiological signal input 308 (e.g., a device coupled directly to the input 308, a device coupled to the input 308 over the network 102, etc.). Thus, the diagnosis engine 302 may retrieve and/or receive any of the patient physiological signals 312 received and/or retrieved by the waveform analysis engine 304. The diagnosis engine 302 is also coupled to the waveform analysis engine 304 and operable to retrieve and/or receive the derived patient signals 314 provided by waveform analysis engine 304. The diagnosis engine 302 is also coupled to the patient information input 310 and operable to retrieve and/or receive patient information 316 from at least one input device that is coupled to the patient monitoring system 300 through the patient information input 308 (e.g., a device coupled directly to the input 310, a device coupled to the input 310 over the network 102, etc.). The diagnosis engine 302 is also coupled to the network input/output 311 and operable to send and/or receive information through the network input/output 311 and over the network 102. The diagnosis engine 302 is also coupled to the display 306 and operable to send patient care recommendations such as, for example, a triage category recommendation 318 and/or an LSI recommendation 320 (discussed in further detail below) to the display 306 and/or another indicator device.

Figure 4:
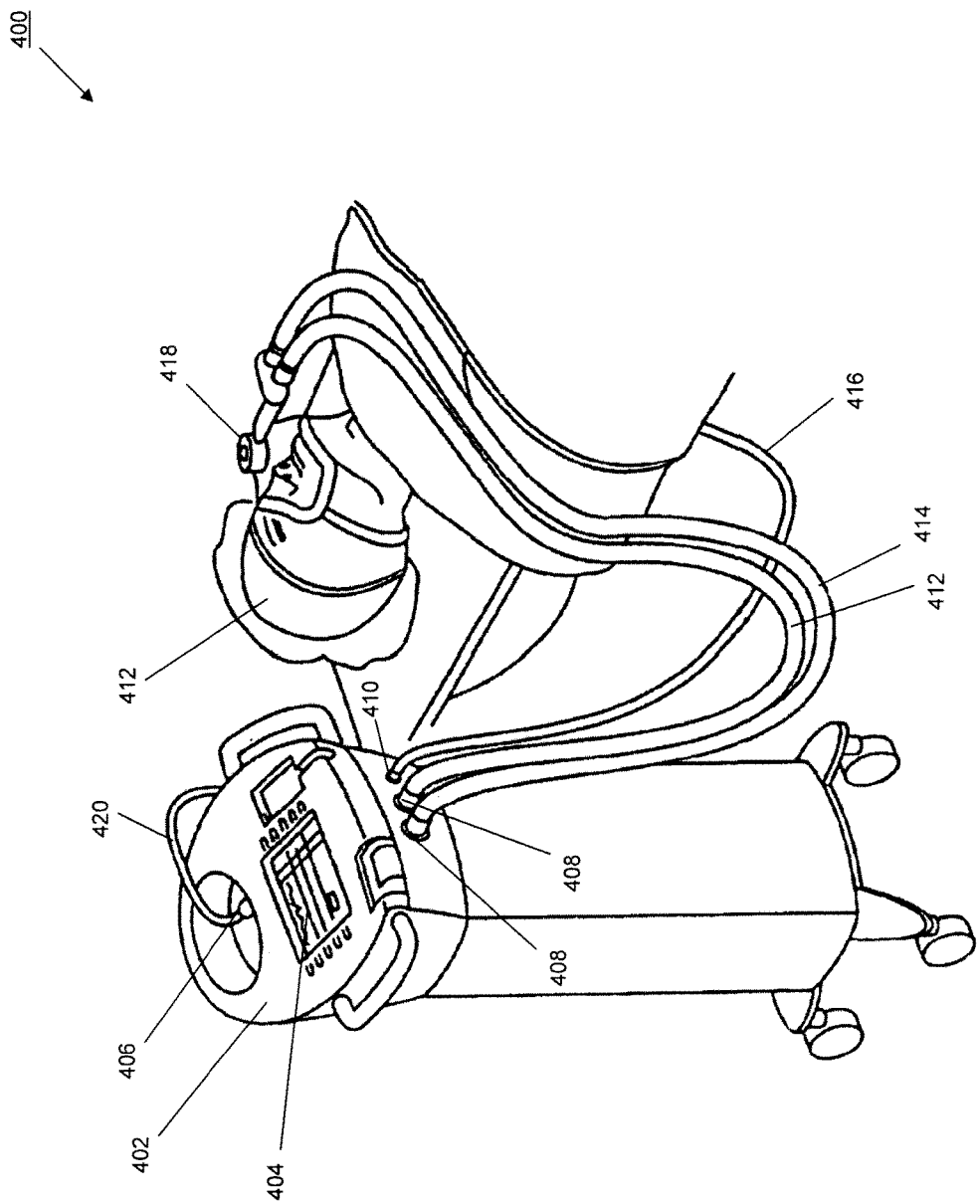
FIG. 4 is a perspective view illustrating an embodiment of the patient monitoring system of FIG. 3 coupled to a patient.

Referring now to FIG. 4, an embodiment of a patient care recommendation system 400 is illustrated that includes some of the components of the patient care recommendation system 100 discussed above with reference to FIG. 1. The patient care recommendation system 400 includes a local patient monitoring system 402 that may be the local patient monitoring system 104 discussed above. In the illustrated embodiment, the local patient monitoring system 402 includes a chassis that houses the components of the patient monitoring system 300, discussed above with reference to FIG. 3, and includes a display/input device 404 (e.g., a touch screen display), a network input/output 406, and a plurality of physiological signal monitoring device inputs 408 and 410. A plurality of couplings 412, 414, and 416 are coupled to the physiological signal monitoring device inputs 408 and 410 and to each of a respiration monitoring device 418, a heart monitoring device (not illustrated), and/or a variety of other physiological signal monitoring devices known in the art to couple a patient 412, which may be the patient 108 discussed above with reference to FIG. 1, to the local patient monitoring device 402. A networking cable 420 is coupled to the network input/output 406 to couple the local patient monitoring device 402 to a network (e.g., the network 102 discussed above with reference to FIG. 1). In an embodiment, the local patient monitoring device 402 is operable to receive patient physiological signals of the patient 412 from the respiration monitoring device 418 and heart monitoring device (not illustrated), receive patient information through the display/input device 404, determine a plurality of derived patient signals from the patient physiological signals, and use the patient information, the patient physiological signals, and the patient derived signals to provide a patient care recommendation on the display/input device 404. In an embodiment, the local patient monitoring device 402 may be operable to send any or all of the patient information, the patient physiological signals, and the patient derived signals over the network to, for example, the remote patient monitoring device 106 discussed above with reference to FIG. 1.

Figure 5:
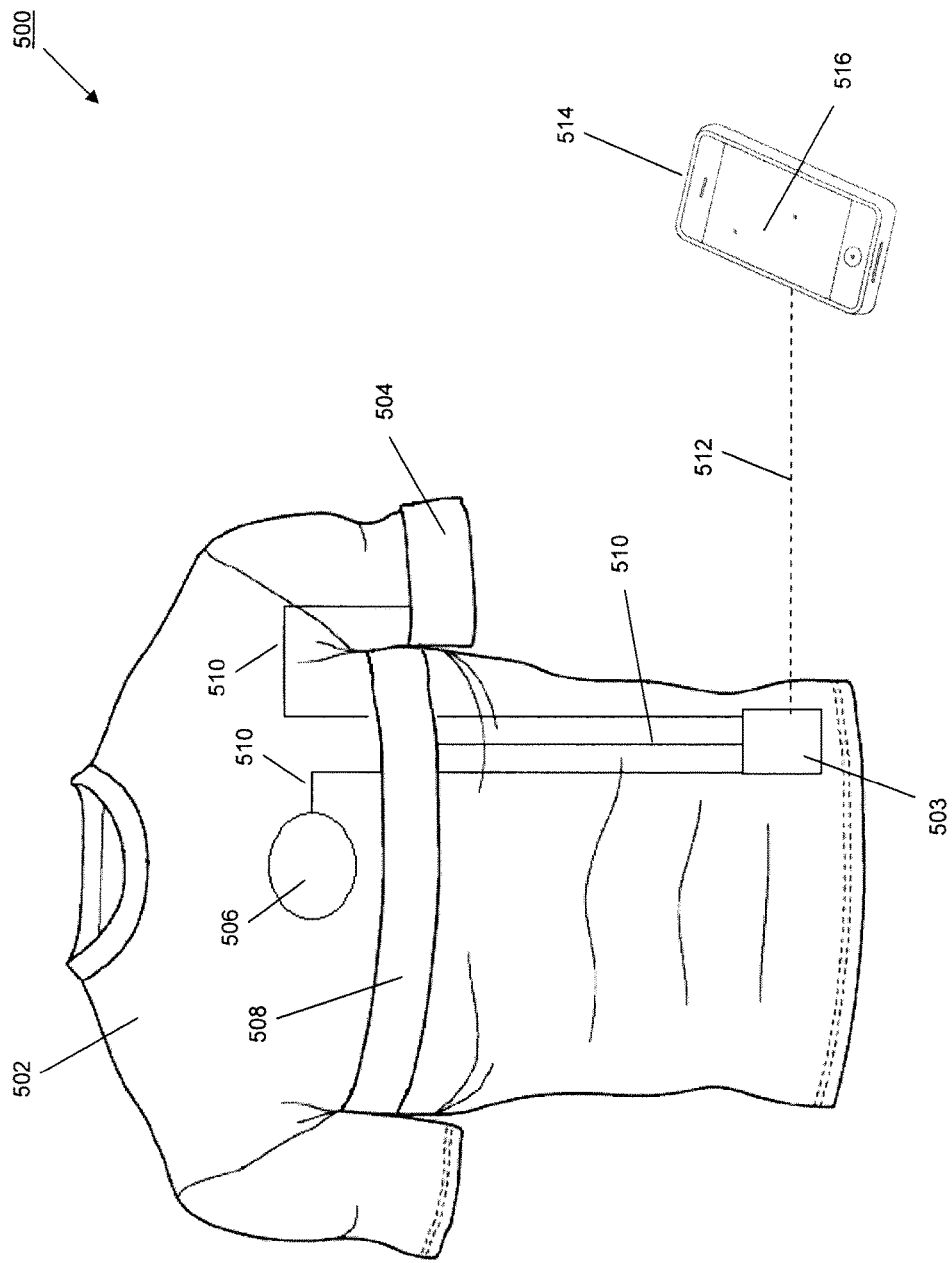
FIG. 5 is a perspective view illustrating an embodiment of the patient monitoring system of FIG. 3 including a local patient monitoring system communicating with a remote patient monitoring system.

Referring now to FIG. 5, another embodiment of a patient care recommendation system 500 is illustrated that includes some of the components of the patient care recommendation system 100 discussed above with reference to FIG. 1. The patient care recommendation system 500 includes a local patient monitoring system 502. In the illustrated embodiment, the local patient monitoring system 502 is included on a shirt or other article or articles of patient wearable clothing that may include components of the local patient monitoring system 104 discussed above with reference to FIG. 1. The local patient monitoring system 502 includes an IHS 503 and a plurality of physiological signal monitoring devices such as a blood pressure monitoring device 504, a heart monitoring device 506, and a respiration monitoring device 508 (e.g., a chest band) that are each coupled to the IHS 503 through respective couplings 510 (e.g., electrical cables) that extend from physiological signal monitoring device inputs on the IHS 503. In an embodiment, a power supply, pressurized air supply (e.g., for the blood pressure monitoring device), and/or a variety of other components may be located on the shirt 503 or coupled to the physiological signal monitoring devices. The IHS 503 also includes a wireless networking device that allows the IHS 503 to wirelessly communicate 512 with a remote patient monitoring device 514 over a network (e.g., the network 102 discussed above with reference to FIG. 1). In an embodiment, the IHS 503 is operable to receive patient physiological signals of a patient wearing the shirt (or otherwise coupled to the blood pressure monitoring device 504, heart monitoring device 506, a respiration monitoring device 508) from the blood pressure monitoring device 504, heart monitoring device 506, a respiration monitoring device 508, and send the patient physiological signals to the remote patient monitoring device 514. The remote patient monitoring device 514 is then operable to receive patient information through a display/input device 516, determine a plurality of derived patient signals from the patient physiological signals, and use the patient information, the patient physiological signals, and the patient derived signals to provide a patient care recommendation on the display/input device 516. In an embodiment, the remote patient monitoring device 514 may be operable to send any or all of the patient information, the patient physiological signals, and the patient derived signals over the network to, for example, another remote patient monitoring device (not illustrated). While a plurality of physical patient care recommendation systems 400 and 500 have been described above, the present disclosure is not limited to these example, and one of skill in the art will recognize that variety of other physical systems will fall within its scope.

Figure 6A:
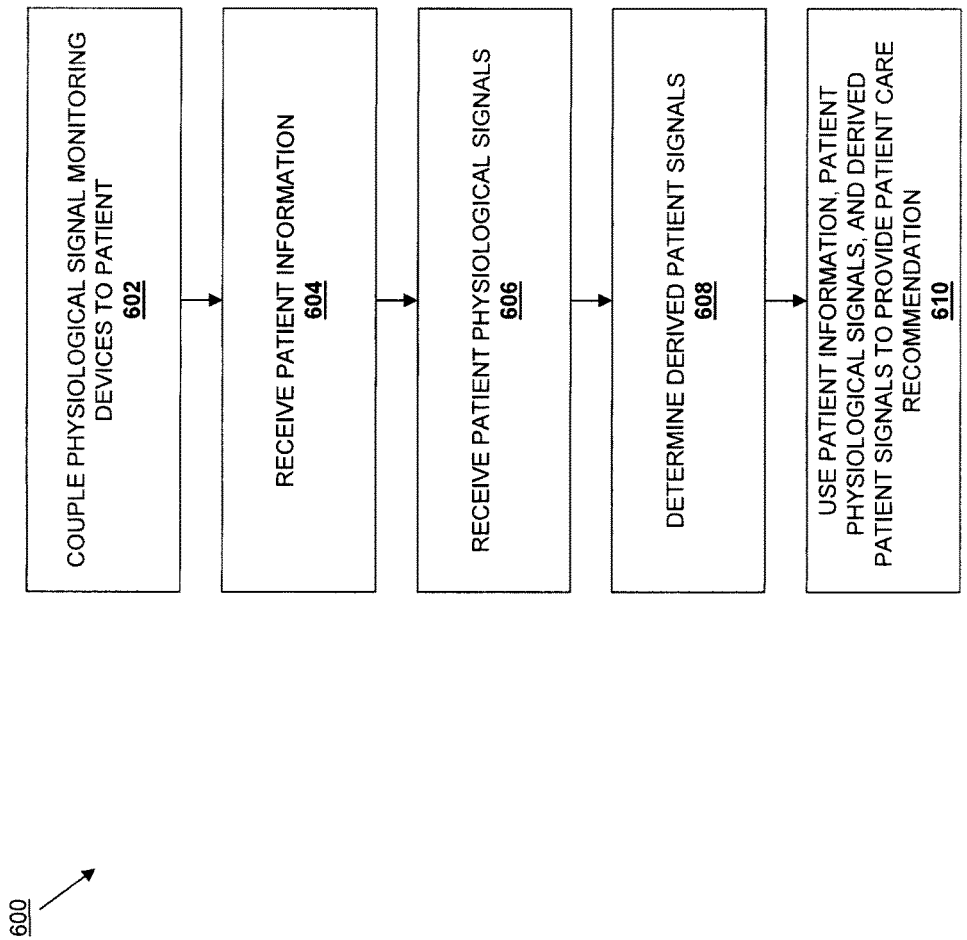
FIG. 6a is a flow chart illustrating an embodiment of a method for providing a patient care recommendation.
Figure 6B:
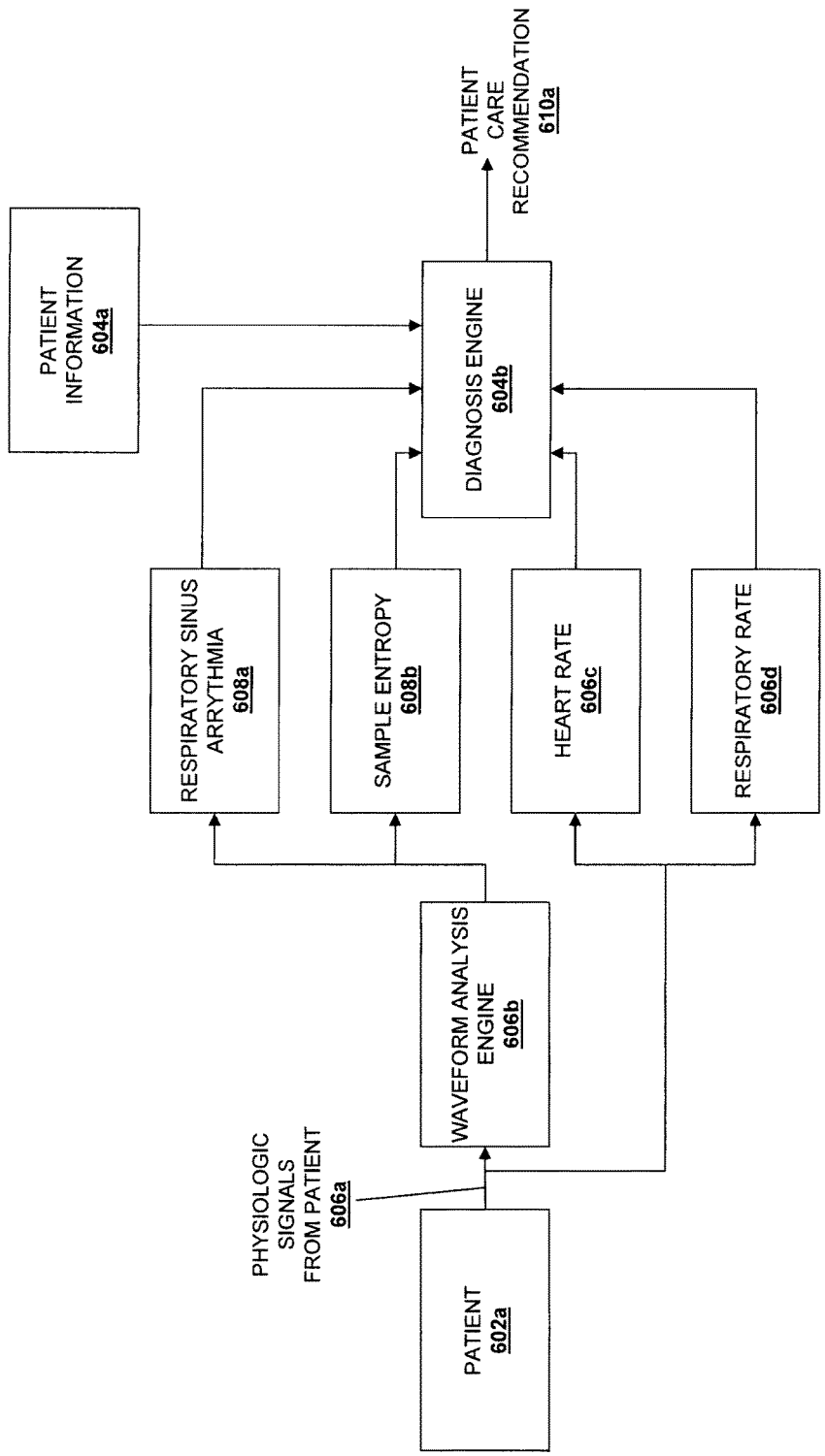
FIG. 6b is a schematic view illustrating an embodiment of the provision of a patient care recommendation.

Referring now to FIGS. 6a and 6b, a method 600 to provide a patient care recommendation is illustrated. The method 600 begins at block 602 where physiological signal monitoring devices are coupled to a patient 602a. In an embodiment, a one or more physiological signal monitoring devices may be coupled to the patient 602a (which may be the patient 108 discussed above with reference to FIG. 1), such as a heart monitoring device, a respiratory monitoring device, a blood pressure monitoring device, and EKG device, and/or a variety of other physiological signal monitoring devices known in the art. For example, a conventional FDA approved vital signs monitor may be used that provides a complete vital signs monitoring solution including heart rate measurements (e.g., numerics and EKG), pulse oximetry, and non-invasive blood pressure (e.g., Systolic, Diastolic, and/or Mean.) In another example, the local patient monitoring system 402, discussed above with reference to FIG. 4, may be coupled to the patient 412. In another example, a patient may wear the local patient monitoring system 502, discussed above with reference to FIG. 5, to couple the blood pressure monitoring device 504, the heart monitoring device 506, and the respiration monitoring device 508 to the patient. One of skill in the art will recognize that a variety of different systems and methods for coupling physiological signal monitoring devices to a patient will fall within the scope of the present disclosure. Furthermore, while only one patient 602a is described as being coupled to physiological signal monitoring devices, any plurality of patients may be coupled to physiological signal monitoring devices such that they may have patient care recommendations provided in the method 600. For example, a plurality of soldiers may be coupled to physiological signal monitoring devices to allow patient care recommendations to be made for those soldiers, a plurality of patients in a hospital or other patient care area may be coupled to physiological signal monitoring devices to allow patient care recommendations to be made for those patients, etc.

The method 600 then proceeds to block 604 where patient information is received. In an embodiment, a doctor, nurse, or other patient care provider may wish to receive a patient care recommendation for the patient 602a from the patient care recommendation system such as, for example, the patient care recommendation systems 100, 400, and/or 500. The doctor, nurse, or other patient care provider may provide patient information 604a about that patient 602a, using an associated input device such as a keyboard, a touch screen, etc., to the diagnosis engine 604b located in the local patient monitoring system coupled to that patient and/or the remote patient monitoring system communicating with a local patient monitoring device coupled to that patient 602a. In an embodiment, patient information 604a about the patient 602a may include patient physical characteristics such as, for example, that patients age, that patients sex, that patients weight, that patients height, and/or a variety of other patient physical characteristics known in the art. Additional patient information may also be provided at block 604 that includes patient scores such as, for example, a Glasgow Coma Score, a Field Triage Score, a Revised Trauma Score, physical exam scores, and/or a variety of other patient scores known in the art. Further patient information may also be provided at block 604 that includes a patient mechanism of injury, patient demographical data, patient disease symptom data, lab findings data, etc. In another embodiment, patient physical characteristics or other patient information for the patient 602a may be stored in an IHS included in the local patient monitoring system (e.g., in the IHS 503 of the local patient monitoring system 500, discussed above with reference to FIG. 5), and those patient physical characteristics or other patient information may be retrieved by or provided to the diagnosis engine 604b located in the remote patient monitoring system (e.g., the remote patient monitoring system 514) in response to a doctor, nurse, or other patient caregiver requesting a patient care recommendation for the patient 602a coupled to that IHS. While a few examples have been provided, one of skill in the art will recognize that a variety of different methods to provide patient information to the patient care recommendation system will fall within the scope of the present disclosure.

The method 600 then proceeds to block 606 where patient physiological signals are received. In an embodiment, the physiological signal monitoring device(s) coupled to the patient in block 602 of the method 600 may continuously or periodically provide patient physiological signals 606a from the patient 602a to the waveform analysis engine 606b and the diagnosis engine 604b located in the local patient monitoring system and/or the remote patient monitoring system. For example, patient heart signals 606c, patient respiratory signals 606d, patient blood pressure signals (not illustrated), patient EKG signals (not illustrated), patient pulse oximetry signals (not illustrated), and/or a variety of other patient physiological signals from the patient 602a may be provided to the waveform analysis engine 606b and the diagnosis engine 604b located in the local patient monitoring system and/or the remote patient monitoring system. In an embodiment, the patient physiological signals may be received and/or retrieved by the waveform analysis engine 606b and the diagnosis engine 604b in real time. In one embodiment, at block 606 of the method 600, patient physiological signals 606a that have been previously stored in a storage device located in the local patient monitoring system and/or the remote patient monitoring system may be retrieved and/or received by the waveform analysis engine 606b and the diagnosis engine 606d located in the local patient monitoring system and/or the remote patient monitoring system.

The method 600 then proceeds to block 608 where derived patient signals are determined. As discussed above, the waveform analysis engine in the local patient monitoring system and/or the remote patient monitoring system is operable to use patient physiological signals to produce derived patient signals (e.g., the RSA signal 608a and the sample entropy signal 608b in the illustrated embodiment). Thus, at block 608 of the method 600, the waveform analysis engine 606b in the local patient monitoring system and/or the remote patient monitoring system uses the patient physiological signals 606a from the physiological signal monitoring devices coupled to the patient 602a to produce one or more of the derived patient signals (e.g., 608a, and 608b) discussed above and provides the derived patient signals to the diagnosis engine 604b.

The method 600 then proceeds to block 610 where the patient information, patient physiological signals, and derived patient signals are used to provide a patient care recommendation. As discussed above, the diagnosis engine in the local patient monitoring system and/or the remote patient monitoring system may be created using trauma patient data and/or other real-world patient data that may include patient physiological signals, derived patient signals, patient information, and/or patient care information, to provide the diagnosis engine 302 with patient care intelligence that allows the diagnosis engine 302 to provide patient care recommendations in response to the inputs provided during the method 600. Thus, at block 610 of the method 600, the diagnosis engine 604b uses the patient care intelligence and the patient information 604a, the patient physiological signals (e.g., 606c and 606d), and/or the derived patient signals (e.g., 608a and 608b), to produce a patient care recommendation 610a. For example, as discussed above, in an embodiment, a trained ANN in the diagnosis engine 302 including the patient care intelligence provided by trauma patient data receives new patient data provided during the method 600 to generate an LSI recommendation, a probability that a patient producing the patient data will require an LSI, etc.

In an embodiment, a patient care recommendation provided by the diagnosis engine may include a variety of different patient care recommendations. As discussed above, a patient care recommendation may include an LSI recommendation produced by the ANN using nodes and learned weights as discussed above. For example, an LSI recommendation may include a recommendation to intubate a patient (e.g., to perform endotracheal intubation on the patient), to perform cardiopulmonary resuscitation on a patient, to perform a chest-tube placement on a patient, to perform a needle chest decompression on a patient, to perform a blood transfusion on a patient, to perform cricothyroidotomy on a patient, to perform a pneumothorax decompression on a patient, to perform hemorrhage control on a patient, to perform fluid resuscitation on a patient, to provide fluids to the patient, to perform a particular operation on the patient, and/or a variety of other LSI recommendations known in the art. In an embodiment, the LSI recommendation may include a value on a predetermined severity scale. For example, a predetermined LSI severity scale may be created that ranges between 0 and 1, 0% and 100%, etc., and the LSI recommendation may include a value within that predetermined LSI severity scale. Thus, the LSI recommendation may include a probability of the need for an LSI (e.g., 0.8, 80%, etc.), a confidence interval for the LSI recommendation (e.g., an indication of the reliability of the value provided on the predetermined LSI severity scale that may depend, for example, on the amount and/or quality of the data—patient information, patient physiological signals, derived patient signals—being used to provide that value), and/or a variety of other predetermined severity scale values known in the art. One of skill in the art will recognize that as more patient information, patient physiological signals, and/or derived patient signals are provided to the system, the accuracy of the LSI recommendation and the degree of confidence in that LSI recommendation may increase.

In an embodiment, an LSI recommendation may be provided by the diagnosis engine using some of the following inputs (which one of skill in the art will recognize may be provided as patient information, patient physiological signals, and/or derived patient signals as discussed above): Total Glasgow Coma Score, Initial Systolic Blood Pressure, Initial Heart Rate, Systolic Blood Pressure Slope (over time), Systolic Blood Pressure Mean (over time), Diastolic Blood pressure Slope (over time), Diastolic Blood Pressure Mean (over time), Mean Arterial Pressure Slope (over time), Mean Arterial Pressure Mean (over time), Saturation of Peripheral Oxygen Slope (over time), Saturation of Peripheral Oxygen Mean (over time), Respiratory Rate Slope (over time), Respiratory Rate Mean (over time), Heart Rate Slope (over time), Heart Rate Mean (over time), Lowest Systolic Blood Pressure, Lowest Diastolic Blood Pressure, Initial Shock Index (HR/SBP), Initial Pulse Pressure (SBP-DBP), and/or a variety of other inputs known in the art.

In another embodiment, a patient care recommendation provided by the diagnosis engine may include a triage category recommendation. In an embodiment, the ANN in the diagnosis engine 302 may be trained to produce triage category recommendations in the same manner as with LSI recommendations discussed above. In another embodiment, the triage category recommendations may be location specific and programmed into the diagnosis engine depending, for example, where the system is used. For example, the patient care intelligence included in the diagnosis engine may be operable to use the patient information received in block 604 of the method 600, the patient physiological signals received in block 606 of the method 600, and/or the derived patient signals received in block 608 of the method to provide a triage category recommendation that indicates how sick, injured, and/or otherwise in need of care a patient is and/or a location that the patient should be taken to receive care. For example, a triage category recommendation may include categories such as, for example, "delayed", "immediate", "minimal", "expectant" (also known to those of skill in the art as DIME), a color coding (e.g., red, yellow, green, and black that correspond to the DIME categories), sick/not sick indications, a value expressing the priority the patient has to be evacuated (e.g., 1, 2, 3, 4 . . . , where 1 is the highest priority for evacuation, 2 is the second highest priority, and so on), and/or a variety of other triage categories known in the art. As discussed above, the diagnosis engine 302 may be trained to determine triage categories, in response to receiving patient data, using trauma patient data. Thus, the triage category recommendation may indicate to a doctor, nurse, or other patient care provider with a true measure of the severity of the patient's current condition. The system may also be preprogrammed with a plurality of locations for treating patients, and the triage category recommendation may include one of those locations.

Figure 6C:
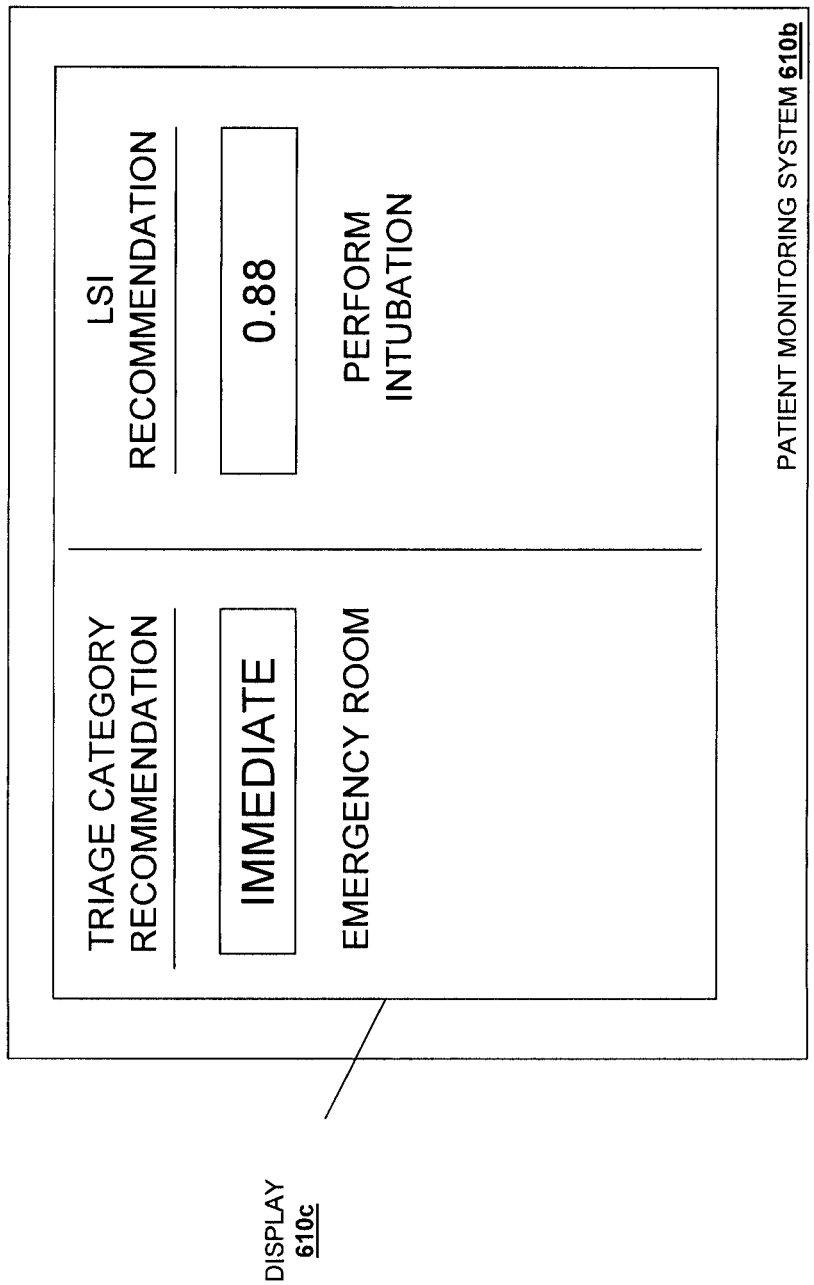
FIG. 6c is a front view illustrating an embodiment of a patient care recommendation displayed on a patient monitoring system.

Referring now to FIG. 6c, a patient monitoring system 610b, which may be a local patient monitoring system and/or a remote patient monitoring system, includes a display 610c that, in the illustrated embodiment, is displaying a patient care recommendation provided by the diagnosis engine. As can be seen, the patient care recommendation includes a triage category of "immediate" (e.g., indicating that the current condition of the patient is severe) with a recommendation that the patient be taken to an emergency room. The patient care recommendation also includes an LSI recommendation that indicates an 88% probability that the patient needs a LSI and a suggestion that the patient be intubated.

Referring now to FIG. 7, a method 700 for providing a patient health determination is illustrated. In an embodiment, the method 700 may be used at block 608 of the method 600, discussed above, to produce at least one of the derived patient signals for use by the diagnosis engine in block 610 of the method 600. However, the method 700 may also be used by itself to produce the patient derived signal that provides a patient health determination that indicates to a doctor, nurse, and/or other patient care provider the health of a patient. The method 700 begins at block 702 where physiological signal monitoring devices are coupled to a patient. At block 702, physiological signal monitoring device may be coupled to a patient in substantially the same manner as discussed above for block 602 of the method 600. Thus, a patient may be coupled to a heart monitoring device, a respiratory monitoring device, an EKG device, etc.

The method 700 then proceeds to blocks 704 and 706 where patient respiratory signals and patient heart signals are received. In an embodiment, a waveform analysis engine may receive respiratory rate signals and heart rate signals from the respiration monitoring device, the heart monitoring device, the EKG device, etc., that are coupled to a patient. In an embodiment, the patient respiratory signals and patient heart signals are received and/or retrieved by the waveform analysis engine with microsecond granularity, e.g., each respective respiratory signal is received within at most 1-5 microseconds of a most recently received patient respiratory signal, and each patient heart signal is received within at most 1-5 microseconds of a most recently received patient heart signal.

The method 700 then proceeds to block 708 where a degree of decoupling between the patient respiratory signals and the patient heart signals is determined. The Applicants of the present disclosure have found that the diagnosis engine may be created such that it is operable to determine a degree of decoupling between patient respiratory signals and patient heart, which the Applicants have found is indicative of patient health, as explained in further detail below.

At any given moment, approximately 10% of the blood in the entire vascular system of a human is distributed to the pulmonary circulation, and 10% of the blood in the pulmonary circulation is distributed to the pulmonary capillary bed. The stroke volume (i.e., the amount of blood ejected into the aorta of a patient during each contraction of the left ventricle) is directly related and may be equivalent to the bolus of blood momentarily circulating in the pulmonary capillary bed. Thus, most of the pulmonary capillary blood volume is replaced with each heartbeat. It follows that the distribution of heartbeats within the respiratory cycle critically affects the efficacy of gas exchange and may be reflective of stroke volume.

During normal conditions the human heart rate is speeding up during inspiration and slowing down during expiration in a phenomenon that is known as respiratory sinus arrhythmia (RSA). RSA is a physiologic adjustment of blood supply to the amount of the available oxygen in the lungs, as when there is oxygen available in the lungs (inspiration), there is a benefit to pump blood through the vessels in the lung to provide the highest exposure of blood to atmospheric air (and oxygen in it) and, conversely, after the blood is oxygenated, to deliver the highest amount of oxygen to the tissues of the body. In addition, RSA conserves energy by slowing down the heart rate such that "unnecessary" (or not efficient from the oxygen uptake point of view) heartbeats are minimized during expiration. RSA is carried out via the action of the parasympathetic autonomic nervous system and there is data to show that the centers responsible for coordination of RSA are in the limbic system of the central nervous system (i.e., the brain).

The RSA has been found to manifest inter-organ influences as the respiration modulates changes in heart rate and the heart rate influences respiration, and the Applicants have determined that particular amounts of coupling, interconnectedness, and/or informational exchange among the cardiac and respiratory systems constitute a state of normal regulation during rest and can be quantified by contemporary statistical analyses that reflect the cardiovascular regulatory complexity. Furthermore, the Applicants have determined that the health of a patient is associated with normal/higher levels of such complexity (e.g., measured as EKG signal irregularity), whereas aging, hemorrhagic shock and other critical states of a patient are associated with lower levels of this complexity. Thus, an RSA signal derived from patient physiological signals is a derived patient signal that can be used to provide a measure of this complexity in a patient, thus allowing a determination of whether the patient is healthy. However, conventional determinations of this complexity require large segments of EKG (about 10-15 minutes of EKG data that is free of mechanical artifacts and rhythm disturbances, both of which are highly likely in patients with critical illness).

During some critical states of a patient such as, for example, hemorrhagic shock, the amount of circulating blood is progressively decreasing, which puts intense demand on the cardio-respiratory regulation to intensify both circulation (i.e., to pump the lessening blood volume through the lungs more frequently in an attempt to maintain the same oxygen delivery to the tissues as was provided prior to the critical state) and respiration (i.e., the increase the respiratory rate and depth to provide more oxygen for contact with blood per individual breath). Furthermore, with increasing respiratory rate, the time available during an inspiration decreases and, in addition, because the volume of blood is decreasing (i.e., due to bleeding), stimulation of the atrial stretch receptors cause an increase in blood pressure which attempts to counteract the predominant trend of decreasing blood pressure due to loss of blood. The Applicants have found that both of the above mechanisms render the variation of heart rate within a respiratory cycle during critical states disadvantageous, and a resulting loss of RSA during such states is detectable, for example, as loss of RRI interval complexity of the EKG and signifies the disappearance of the normal coupling or inter-organ communications between the cardio-vascular and respiratory systems which, in turn, signifies a state of reduced cardiovascular regulatory complexity. Thus, the detection of the decoupling of heart signals and respiratory signals that is indicated by a diminishing or absent RSA provides an early, non-invasive marker of decreased complexity that indicates a decreased level of health of a patient.

In one embodiment, the RSA has been quantified by the Applicants using a simple approach within each respiratory cycle (or consecutive cycles) of the patient. For example, one method to provide noninvasive RSA estimation includes a 10 second (or one respiratory cycle long) EKG tracing of the patient. This is followed by a determination of the length of the R-to-R interval (RRI) (e.g., in milliseconds) within the EKG segment being used. A respiratory tracing that identifies the occurrence of inspiration and expiration in then obtained. The length of the RRI (e.g., in milliseconds) within one respiratory cycle during inspiration ($RRI_I$) is then be determined and divided by the length of the RRI during expiration ($RRI_E$). The Applicants have found that a ratio of the $RRI_I/RRI_E \leq 1$ constitutes the presence of RSA in the patient that signifies normal levels of coupling of the cardiovascular and respiratory interactions and thus normal levels of complexity indicating a normal level of health in the patient, while a ratio of the $RRI_I/RRI_E \geq 1$ constitutes the absence of RSA and signifies a disappearance or decoupling of cardio-vascular and respiratory interactions indicating a decreasing complexity and a decreased level of health in the patient that may be detected very early in the critical state of the patient. While one method of quantifying the RSA to provide a derived patient signal or patient health determination has been described, one of skill in the art will recognize that a variety of other methods for quantifying the RSA in a patient will fall within the scope of the present disclosure.

Thus, at block 708 of the method 700, the presence or degree of RSA in a patient may be used as a forewarning of exhaustion of the normal compensatory reserves of the patient during trauma, hemorrhage, and/or a variety of other critical patient conditions known in the art, as normal high levels of complexity indicate good health and a loss of complexity provides an early indication of a loss of health by indicating a degree of decoupling between the respiratory system and the cardiovascular system of the patient relative to a coupling that exists between the respiratory system and the cardiovascular system of the patient when the patient is healthy.

Thus, the diagnosis engine may be created with patient care intelligence, as discussed above, to be operable to interpret normal states of complexity indicated by the RSA detected in a patient as derived patient signals that signify health, while interpreting decreases in complexity indicated by the RSA detected in a patient as derived patient signals that signify the loss of ability of the patient to withstand the patients condition, a poor prognosis, and/or a forewarning of physiologic deterioration in the patient. For example, the waveform analysis engine may use the patient heart signals and the patient respiratory signals to calculate the patient RSA signals as the ratio of the heart interbeat interval of the patient during inspiration by the patient to the heart interbeat interval of the patient during expiration by the patient. Those patient RSA signals may then be sent to the diagnosis engine, which may be operable to interpret the patient RSA signals to signify that a patient is healthy if the RSA signals (e.g., the RRI ratio discussed above) are less than 1 (and thus at a normal state of complexity and unstrained in compensating for the condition of the patient), and to interpret the patient RSA signals to signify early signs of depletion of the normal compensatory reserves of the patient if the RSA signals are equal to or greater than 1. In an embodiment, a degree of decoupling indicated by the patient RSA signals may be associated with physiological signs of instability of the patient in a database that is coupled to or otherwise accessible by the diagnosis engine. The degree of decoupling between the respiratory system of the patient and the cardiovascular system of the patient expressed as the patient RSA signals may further be associated with triage category recommendation and LSI recommendations, as discussed above.

The method 700 then proceeds to block 710 where a patient health indicator is provided that is based on the degree of decoupling of the patient respiratory signals and the patient heart signals. In an embodiment, the diagnosis engine may provide the patient RSA signals or another patient health indicator, that is based on the degree of decoupling between the patient respiratory signals and the patient heart signals indicated by the patient RSA signals, to a display or other indicator device. For example, the ratio of the $RRI_I/RRI_E$ discussed above may be displayed on a display and interpretable by a patient care provider as a value that indicates the health of a patient. In another embodiment, the diagnosis engine may use the RSA signal with patient information (e.g., patient physical characteristics) and patient physiological signals to provide a patient health indicator that may be part of the patient care recommendation provided in the method 600 and described above. Thus, a doctor, nurse, and/or other patient care provider may use the patient health indicator to determine the health of a patient, or the patient health indicator may be used by a patient monitoring system to provide a patient care recommendation to the doctor, nurse, and/or other patient care provider.

In another embodiment, patient derived signals determined at block 608 of the method 600 and used at block 610 to provide the patient care recommendation may include a sample entropy signal, as discussed above. Sample entropy measures the regularity of a nonlinear time series data by examining the data for similar epochs (i.e., groups of consecutive points of similar lengths) in which more frequent and similar epochs yield lower values of the sample entropy. In experimental embodiments, sample entropy applied to patient physiological signals have been found to allow the comparison of patterns in the patient physiological signals to determine the complexity of those patterns in relatively short datasets (e.g., datasets of 100 heartbeats in length). In one experimental embodiment, sample entropy signals were created to measure the amount of irregularity in the R-R interval signal from an EKG device coupled to a patient and found to provide an accurate predicator of the degree of success in separating that patient from mechanical ventilation. One of skill in the art will recognize that the sample entropy of a variety of patient physiological signals may be calculated and provided as a derived patient signal to the diagnosis engine. Furthermore, the patient care intelligence in the diagnosis engine may allow the diagnosis engine to provide specific and accurate patient care recommendations based on sample entropy values created from a variety of different patient physiological signals.

Thus, a system and method are described that allow patient care recommendations to be provided for one or more patients quickly, accurately, and non-invasively. The systems and methods may be practiced in several different situations while remaining within the scope of the present disclosure. For example, the systems and methods discussed above may be incorporated into a hospital or other patient care facility (e.g., emergency rooms, intensive care units, operating rooms, step down units), a en-route care vehicle for transporting a patient to a patient care facility (e.g., helicopters, ground ambulances, etc.), a battlefield situation or other mass casualty/injury situation, a mobile device carried by a single patient that is monitored remotely by a care provider, and/or a variety of other situations known in the art. In battlefield situations, the absence of frequent physiological measurements from the wounded soldiers forces battlefield medics and hospital personnel to make rapid decisions about priority of care and application of LSIs based upon isolated "snapshot" data points (e.g., blood pressure, pulse character, respiratory rate, and mental status), while the system and methods of the present disclosure allow the quick and accurate observation and analysis of trends and the dynamic nature of the evolving and possibly critically injured physiology of the patient by continuously providing and analyzing patient physiological signals and advanced patient vital signs (i.e. derived patient signals).

While the systems and methods described above are particularly applicable to the critically ill and/or injured, they should not be limited to such patient's, as one of skill in the art will recognize that the systems and methods described above will provide benefits for patient's requiring all levels of care. Furthermore, the system and method described provides for the remote monitoring of the health of a plurality of patients and the determination of patient care for that plurality of patients. For example, each of a plurality of patients may be coupled to a respective local patient monitoring system as discussed above, and a remote patient monitoring system may monitor the health of that plurality of patients through the transmittal of their respective patient physiological signals from their local patient monitoring systems. Furthermore, the remote patient monitoring system may provide patient care recommendations for each of the patients using the techniques discussed above, and the user of the remote patient monitoring system may direct patient care providers to provide patient care (using, for example, the LSI recommendation) for each of the patients. One of skill in the art will recognize that such an embodiment may be particularly useful in patient management for a large hospital, or for providing patient care to a plurality of soldiers on a battlefield.

Although illustrative embodiments have been shown and described, a wide range of modification, change and substitution is contemplated in the foregoing disclosure and in some instances, some features of the embodiments may be employed without a corresponding use of other features. Accordingly, it is appropriate that the appended claims be construed broadly and in a manner consistent with the scope of the embodiments disclosed herein.

What is claimed is:

1. A patient health determination system, comprising:
a respiration monitoring device that is operable to provide a plurality of patient respiratory signals related to a patient;
a heart monitoring device that is operable to provide a plurality of patient heart signals related to the patient; and
a diagnosis engine coupled to the respiration monitoring device and the heart monitoring device, wherein the diagnosis engine is programmed to:
receive the plurality of patient respiratory signals from the respiration monitoring device;
receive the plurality of patient heart signals from the heart monitoring device;
determine a degree of decoupling, where the degree of decoupling is determined based on a ratio of a length of a R-to-R interval within one inspiration cycle to a length of a R-to-R interval within one expiration cycle in an electrocardiography waveform, wherein the R-to-R interval within one inspiration cycle and the R-to-R interval within one expiration cycle are obtained from one respiratory cycle; and
provide a patient health indicator based on only the degree of decoupling between the plurality of patient respiratory signals and the plurality of patient heart signals; and
wherein the patient health indicator provides an indication of a need for life saving intervention by medical personnel.

2. The system of claim 1, wherein each of the plurality of patient respiratory signals is received by the diagnosis engine within at most 5 microseconds of a most recently received patient respiratory signal.

3. The system of claim 1, wherein each of the plurality of patient heart signals is received by the diagnosis engine with a granularity of at most 5 microseconds.

4. The system of claim 1, wherein the degree of decoupling determined between the plurality of patient respiratory signals and the plurality of patient heart signals is relative to a coupling between the plurality of patient respiratory signals and the plurality of patient heart signals that exists in a healthy patient.

5. The system of claim 1, wherein the degree of decoupling between the plurality of patient respiratory signals and the plurality of patient heart signals is associated with a physiological sign of instability in a database that is coupled to the diagnosis engine.

6. The system of claim 1, wherein the diagnosis engine determines the degree of decoupling between the plurality of patient respiratory signals and the plurality of patient heart signals by performing a calculation on at least some of the plurality of patient respiratory signals and at least some of the plurality of patient heart signals.

7. The system of claim 1, further comprising:
a display coupled to the diagnosis engine and operable to display the patient health indicator.

8. A non-transitory computer-readable medium comprising computer-readable instructions to provide a patient health determination, said computer-readable instructions comprising instructions that, when executed by a processor, cause the processor to:
retrieve a plurality of patient respiratory signals from a respiration monitoring device;
retrieve a plurality of patient heart signals from a heart monitoring device;
determine a degree of decoupling, where the degree of decoupling is determined based on a ratio of a length of a R-to-R interval within one inspiration cycle to a length of a R-to-R interval within one expiration cycle in an electrocardiography waveform; and
provide a patient health indicator based only on the degree of decoupling between the plurality of patient respiratory signals and the plurality of patient heart signals; and
wherein the patient health indicator provides an indication of a need for life saving intervention by medical personnel.

9. The non-transitory computer-readable medium of claim 8, wherein the instructions, when executed by a processor, cause the processor to:

retrieve each of the plurality of patient respiratory signals within at most 5 microseconds of a most recently retrieved patient respiratory signal.

10. The non-transitory computer-readable medium of claim 8, wherein the plurality of patient heart signals have a granularity of 5 microseconds or less.

11. The non-transitory computer-readable medium of claim 8, wherein the degree of decoupling determined between the plurality of patient respiratory signals and the plurality of patient heart signals is relative to a coupling between the plurality of patient respiratory signals and the plurality of patient heart signals that exists in a healthy patient.

12. The non-transitory computer-readable medium of claim 8, wherein the degree of decoupling between the plurality of patient respiratory signals and the plurality of patient heart signals is associated with a physiological sign of instability in a database that is coupled to the processor.

13. The non-transitory computer-readable medium of claim 8, wherein the instructions, when executed by a processor, that cause the processor to determine the degree of decoupling between the plurality of patient respiratory signals and the plurality of patient heart signals further include instructions that cause the processor to:
    perform a calculation on at least some of the plurality of patient respiratory signals and at least some of the plurality of patient heart signals.

14. The non-transitory computer-readable medium of claim 8, wherein the instructions, when executed by a processor, cause the processor to:
    provide the patient health indicator to a display.

15. A method to provide a patient health determination, comprising:
    receiving in at least a waveform analysis engine a plurality of patient respiratory signals from a respiration monitoring device that is coupled to a patient;
    receiving in at least the waveform analysis engine a plurality of patient heart signals from a heart monitoring device that is coupled to the patient;
    determining a degree of decoupling with at least one of the waveform analysis engine and a diagnosis engine, where the degree of decoupling is determined based on a ratio of a length of a R-to-R interval within one inspiration cycle to a length of a R-to-R interval within one expiration cycle in an electrocardiography waveform, wherein the R-to-R interval within one inspiration cycle and the R-to-R interval within one expiration cycle are obtained from one respiratory cycle; and
    providing with the diagnosis engine a patient health indicator to an indicator device, wherein the patient health indicator is based only on the degree of decoupling between the plurality of patient respiratory signals and the plurality of patient heart signals; and
    wherein the patient health indicator provides an indication of a need for life saving intervention by medical personnel.

16. The method of claim 15, further comprising:
    receiving each of the plurality of patient respiratory signals within at most 5 microseconds of a most recently received patient respiratory signal; and
    receiving each of the plurality of patient heart signals within at most 5 microseconds of a most recently received patient heart signal.

17. The method of claim 15, wherein the degree of decoupling determined between the plurality of patient respiratory signals and the plurality of patient heart signals is relative to a coupling between the plurality of patient respiratory signals and the plurality of patient heart signals that exists in a healthy patient.

18. The method of claim 15, wherein the degree of decoupling between the plurality of patient respiratory signals and the plurality of patient heart signals is associated with a physiological sign of instability that is retrieved from a database.

19. The method of claim 15, wherein the determining the degree of decoupling includes:
    performing a calculation on at least some of the plurality of patient respiratory signals and at least some of the plurality of patient heart signals.

20. The method of claim 15, wherein the indicator device is a display device.

21. The computer-readable medium of claim 8, wherein the degree of decoupling is determined to exist when a ratio of the length of the R-to-R interval within one inspiration cycle to the length of the R-to-R interval within one expiration cycle in an electrocardiography waveform is greater than or equal to 1.

22. The method of claim 15, further comprising receiving patient information; and
    wherein the patient health indicator is based on the received patient information.

* * * * *